United States Patent
Fonacier et al.

(10) Patent No.: US 8,562,565 B2
(45) Date of Patent: Oct. 22, 2013

(54) BATTERY SHOCK ABSORBER FOR A PORTABLE MEDICAL DEVICE

(75) Inventors: Ejmar Fonacier, Woodland Hills, CA (US); Kirk A. Allen, Valencia, CA (US); Chad Srisathapat, Sun Valley, CA (US); Afshin Bazargan, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 307 days.

(21) Appl. No.: 12/905,931

(22) Filed: Oct. 15, 2010

(65) Prior Publication Data

US 2012/0095398 A1    Apr. 19, 2012

(51) Int. Cl.
*A61M 1/00*    (2006.01)

(52) U.S. Cl.
USPC .......................................... 604/151

(58) Field of Classification Search
USPC ........ 604/65–67, 131, 151; 429/181, 185, 53, 429/82; 362/204, 205
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,305 A * | 3/1988 | Goebel et al. .......... 429/94 |
| 4,731,726 A | 3/1988 | Allen, III |

(Continued)

FOREIGN PATENT DOCUMENTS

DE    4329229    3/1995
EP    0319268    11/1988

(Continued)

OTHER PUBLICATIONS

PCT Search Report (PCT/US02/03299), Oct. 31, 2002, Medtronic Minimed, Inc.

(Continued)

*Primary Examiner* — Manuel Mendez
(74) *Attorney, Agent, or Firm* — Ingrassia Fisher & Lorenz, P.C.

(57) ABSTRACT

A device for delivering fluid to a user includes a housing, a drive motor assembly in the housing, other internal components in the housing, and a keypad external to the housing. The device includes a number of features and elements that enhance its operation, manufacturability, reliability, and user-friendliness. These features and elements include a shock absorbing element for a battery of the device, a keypad actuator layer that overlies a keypad assembly and forms a water resistant seal with the housing, and an offset element for a piezoelectric speaker that is located inside the housing.

20 Claims, 24 Drawing Sheets

(56) References Cited

U.S. PATENT DOCUMENTS

| | | |
|---|---|---|
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,207,645 A * | 5/1993 | Ross et al. .................. 604/141 |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,137,890 A | 10/2000 | Markow |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |

(56) References Cited

U.S. PATENT DOCUMENTS

| | | | |
|---|---|---|---|
| 6,728,576 | B2 | 4/2004 | Thompson et al. |
| 6,733,471 | B1 | 5/2004 | Ericson et al. |
| 6,746,582 | B2 | 6/2004 | Heller et al. |
| 6,747,556 | B2 | 6/2004 | Medema et al. |
| 6,749,740 | B2 | 6/2004 | Liamos et al. |
| 6,752,787 | B1 | 6/2004 | Causey, III et al. |
| 6,809,653 | B1 | 10/2004 | Mann et al. |
| 6,817,990 | B2 | 11/2004 | Yap et al. |
| 6,881,551 | B2 | 4/2005 | Heller et al. |
| 6,892,085 | B2 | 5/2005 | McIvor et al. |
| 6,893,545 | B2 | 5/2005 | Gotoh et al. |
| 6,895,263 | B2 | 5/2005 | Shin et al. |
| 6,916,159 | B2 | 7/2005 | Rush et al. |
| 6,932,584 | B2 | 8/2005 | Gray et al. |
| 6,932,894 | B2 | 8/2005 | Mao et al. |
| 6,942,518 | B2 | 9/2005 | Liamos et al. |
| 7,153,263 | B2 | 12/2006 | Carter et al. |
| 7,153,289 | B2 | 12/2006 | Vasko |
| 7,396,330 | B2 | 7/2008 | Banet et al. |
| 7,621,893 | B2 | 11/2009 | Moberg et al. |
| 8,089,198 | B2 | 1/2012 | Bianchini |
| 2001/0044731 | A1 | 11/2001 | Coffman et al. |
| 2002/0013518 | A1 | 1/2002 | West et al. |
| 2002/0055857 | A1 | 5/2002 | Mault et al. |
| 2002/0082665 | A1 | 6/2002 | Haller et al. |
| 2002/0137997 | A1 | 9/2002 | Mastrototaro et al. |
| 2002/0161288 | A1 | 10/2002 | Shin et al. |
| 2003/0016211 | A1 | 1/2003 | Woolley |
| 2003/0060765 | A1 | 3/2003 | Campbell et al. |
| 2003/0078560 | A1 | 4/2003 | Miller et al. |
| 2003/0088166 | A1 | 5/2003 | Say et al. |
| 2003/0144581 | A1 | 7/2003 | Conn et al. |
| 2003/0152823 | A1 | 8/2003 | Heller |
| 2003/0176183 | A1 | 9/2003 | Drucker et al. |
| 2003/0188427 | A1 | 10/2003 | Say et al. |
| 2003/0199744 | A1 | 10/2003 | Buse et al. |
| 2003/0208113 | A1 | 11/2003 | Mault et al. |
| 2003/0220552 | A1 | 11/2003 | Reghabi et al. |
| 2004/0061232 | A1 | 4/2004 | Shah et al. |
| 2004/0061234 | A1 | 4/2004 | Shah et al. |
| 2004/0064133 | A1 | 4/2004 | Miller et al. |
| 2004/0064156 | A1 | 4/2004 | Shah et al. |
| 2004/0073095 | A1 | 4/2004 | Causey, III et al. |
| 2004/0074785 | A1 | 4/2004 | Holker et al. |
| 2004/0093167 | A1 | 5/2004 | Braig et al. |
| 2004/0097796 | A1 | 5/2004 | Berman et al. |
| 2004/0102683 | A1 | 5/2004 | Khanuja et al. |
| 2004/0111017 | A1 | 6/2004 | Say et al. |
| 2004/0122353 | A1 | 6/2004 | Shahmirian et al. |
| 2004/0167465 | A1 | 8/2004 | Mihai et al. |
| 2004/0263354 | A1 | 12/2004 | Mann et al. |
| 2005/0038331 | A1 | 2/2005 | Silaski et al. |
| 2005/0038680 | A1 | 2/2005 | McMahon et al. |
| 2005/0154271 | A1 | 7/2005 | Rasdal et al. |
| 2005/0192557 | A1 | 9/2005 | Brauker et al. |
| 2006/0228623 | A1* | 10/2006 | Ebi et al. ............... 429/181 |
| 2006/0229694 | A1 | 10/2006 | Schulman et al. |
| 2006/0238333 | A1 | 10/2006 | Welch et al. |
| 2006/0293571 | A1 | 12/2006 | Bao et al. |
| 2007/0088521 | A1 | 4/2007 | Shmueli et al. |
| 2007/0135866 | A1 | 6/2007 | Baker et al. |
| 2008/0154503 | A1 | 6/2008 | Wittenber et al. |
| 2008/0294065 | A1 | 11/2008 | Waldhoff et al. |
| 2009/0034776 | A1 | 2/2009 | Angelis et al. |
| 2009/0081951 | A1 | 3/2009 | Erdmann et al. |
| 2009/0082635 | A1 | 3/2009 | Baldus et al. |
| 2009/0270810 | A1 | 10/2009 | DeBelser et al. |
| 2010/0246863 | A1 | 9/2010 | Onishi et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy, The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.

(56) References Cited

OTHER PUBLICATIONS (MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequisite of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al. "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

(56) References Cited

OTHER PUBLICATIONS

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

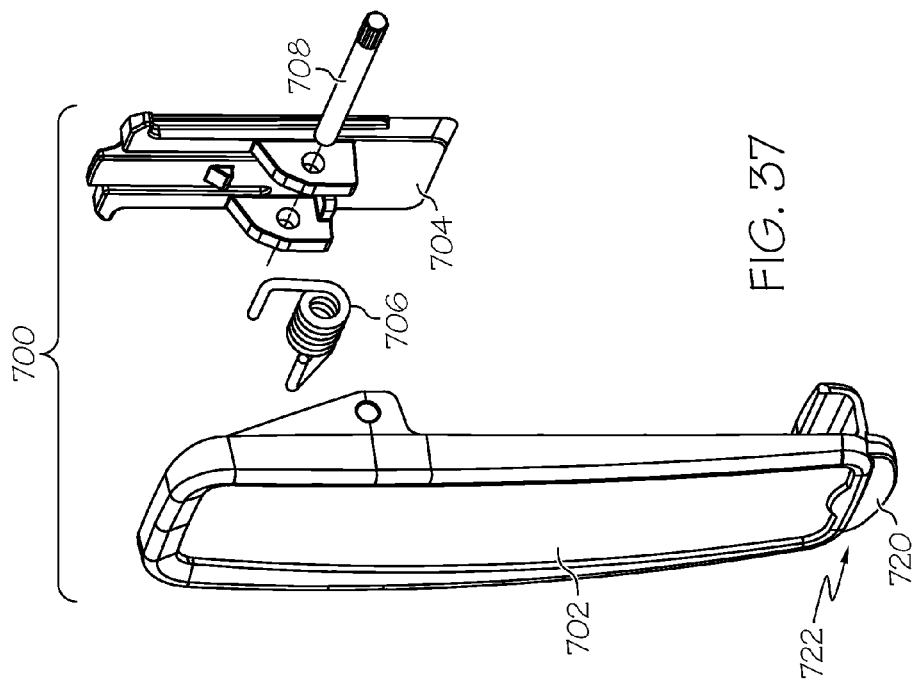
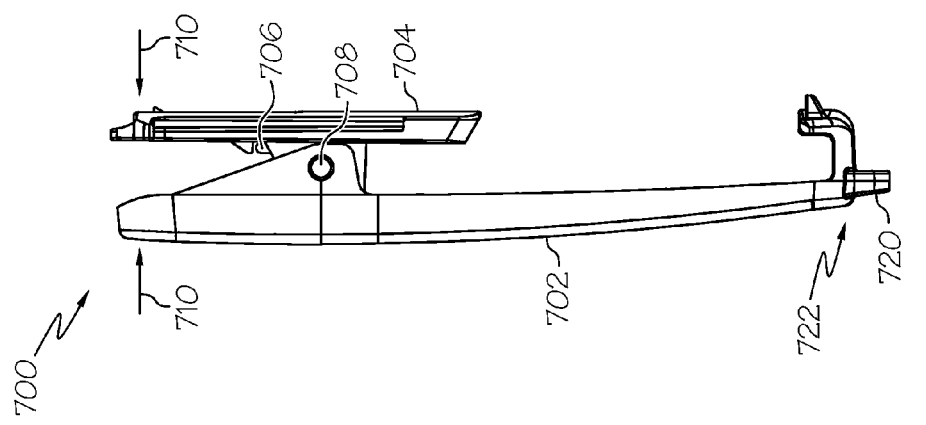

BATTERY SHOCK ABSORBER FOR A PORTABLE MEDICAL DEVICE

CROSS-REFERENCE TO RELATED APPLICATIONS

The subject matter described here is related to the subject matter described in U.S. patent application Ser. Nos. 12/905,933, and 12/905,936, both filed on Oct. 15, 2010.

TECHNICAL FIELD

Embodiments of the subject matter described herein relate generally to medical devices such as fluid infusion devices. More particularly, embodiments of the subject matter relate to subassemblies, packaging features, and housing features of a personal insulin infusion pump.

BACKGROUND

Portable medical devices are useful for patients that have conditions that must be monitored on a continuous or frequent basis. For example, diabetics are usually required to modify and monitor their daily lifestyle to keep their body in balance, in particular, their blood glucose (BG) levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin) In lieu of a syringe, the patient can simply activate the insulin pump to administer an insulin bolus as needed, for example, in response to the patient's current BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a stopper in a reservoir. The fluid containment assembly typically includes the reservoir with the stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

Personal medical devices such as infusion pumps are typically powered by a battery or battery pack. For example, some medical devices can be powered by a single AA battery. The portable nature of such devices means that they might be subjected to physical impact, shock, or stress (which may result from physical activity of the user, accidental bumping into nearby objects, dropping of the device, etc.). The force imparted by a battery to the housing of a portable medical device could compromise the integrity of the housing and/or disturb the delicate operating components inside the housing. Accordingly, it is desirable to have a feature or component that protects the battery, the housing, and/or other elements of a medical device from battery impacts.

A number of electronic devices, including personal medical devices such as infusion pumps, include membrane keypad assemblies that allow the user to manipulate certain functions of the devices. Conventional membrane keypad assemblies usually include an underlying keypad layer and an overlying actuator layer. The bottom surface of the actuator layer is typically printed with graphics associated with the different keys or buttons and/or with decorative graphics. The actuator layer is usually attached to the keypad layer or the housing of the device using an adhesive or bonding material. Ideally, the actuator layer is sealed around the housing such that moisture and contaminants cannot enter the housing. Indeed, some personal medical devices are designed to be water resistant (to accommodate bathing, swimming, exposure to rain, etc.) and, for such devices, the actuator layer forms a water resistant seal with the housing. In this regard, it is desirable to have a membrane keypad assembly that exhibits strong, robust, and reliable water resistant characteristics.

Many electronic devices, including personal medical devices such as infusion pumps, use piezoelectric speakers to generate sound. If the device is waterproof or water resistant, then a piezoelectric speaker will typically be mounted against the inner wall of the housing for purposes of transmitting sound to the outside world. For such implementations, the volume of sound produced by the piezoelectric speaker will be influenced by various factors such as the shape, size, and structural features of the housing. If a piezoelectric speaker is mounted directly to a rigid case or housing of a device, however, it will not effectively or efficiently generate sound at the desired volume. Accordingly, it is desirable to have a piezoelectric speaker assembly that operates effectively when mounted within a sealed rigid housing of an electronic device.

BRIEF SUMMARY OF EMBODIMENTS

A shock absorbing element for a battery of a medical device is provided. The medical device includes a battery receptacle for the battery and an electrical contact for the battery. The electrical contact resides within the battery receptacle, and the shock absorbing element is composed of a resilient material. The shock absorbing element includes: a perimeter sized and shaped to accommodate placement in the battery receptacle; a through hole formed in the resilient material, the through hole being sized and shaped to accommodate the electrical contact; a first side; a second side; and shock absorbing features formed on the first side or the second side to dissipate kinetic energy associated with motion of the battery relative to the battery receptacle.

Also provided is a shock absorbing assembly for a battery of a medical device. The shock absorbing assembly includes: a battery sleeve to house the battery, the battery sleeve having a base end; an electrical contact for the battery, the electrical contact residing within the battery sleeve near the base end; and a shock absorbing element located within the battery sleeve near the base end, the shock absorbing element composed of a resilient material having shock absorbing features integrally formed therein to dissipate kinetic energy associated with motion of the battery toward the base end.

A portable medical device is also provided. The portable medical device includes: a housing; a battery sleeve inside the housing, the battery sleeve having a base end, wherein the battery sleeve accommodates a battery for the portable medical device; a battery contact located inside the battery sleeve near the base end; and a resilient and compressive element located inside the battery sleeve near the base end, the battery contact protruding through the resilient and compressive element, wherein the resilient and compressive element dissipates kinetic energy associated with motion of the battery toward the base end.

A medical device according to an embodiment is provided. The medical device includes: a housing having a front face, a keypad mounting area on the front face, and a sealing surface on the front face, the sealing surface surrounding the keypad mounting area; a membrane keypad assembly coupled to the keypad mounting area, the membrane keypad assembly comprising a plurality of actuation components integrated therein; a sealing element overlying the membrane keypad assembly and coupled to the sealing surface to form a fluid resistant seal with the housing; and a graphic keypad overlay adhered to the sealing element, the graphic keypad overlay comprising graphical representations corresponding to the actuation components.

Also provided is a case assembly for a medical device. The case assembly includes: a plastic housing having a keypad mounting cavity and a sealing rim integrally formed therein, the sealing rim located outside and around the keypad mounting cavity; a membrane keypad assembly positioned in the keypad mounting cavity, the membrane keypad assembly comprising a plurality of actuation elements; and a plastic actuator layer overlying the membrane keypad assembly and comprising a plurality of protrusions corresponding to the actuation elements and further comprising a perimeter area that extends beyond the membrane keypad assembly. The perimeter area is attached to the sealing rim to form a fluid resistant seal between the plastic housing and the plastic actuator layer.

A method of manufacturing a medical device is also provided. The method begins by providing a plastic housing having a keypad mounting area and a sealing rim positioned outside the keypad mounting area. The method continues by affixing a membrane keypad assembly on the keypad mounting area, the membrane keypad assembly comprising a plurality of actuation elements. The perimeter area of a plastic actuator layer is sealed to the sealing rim to form a fluid resistant seal between the plastic housing and the plastic actuator layer, wherein the plastic actuator layer overlies the membrane keypad assembly, and wherein protrusions formed on the plastic actuator layer are aligned with the actuation elements of the membrane keypad assembly.

Another embodiment of a medical device is also provided. The medical device includes: a rigid housing having an interior surface; a piezoelectric speaker enclosed within the rigid housing, the piezoelectric speaker comprising an actuator that is controlled to generate sound during operation of the medical device; and an offset element located between the interior surface and the actuator. The offset element, the actuator, and the interior surface at least partially define a resonant cavity for the piezoelectric speaker.

Also provided is a transducer assembly for a medical device having a rigid housing and a flat interior surface. The transducer assembly includes: a piezoelectric speaker comprising an actuator; and an offset element for the piezoelectric speaker. The offset element has an actuator side that mates with the piezoelectric speaker, a housing side that mates with the flat interior surface of the rigid housing, and an opening formed therein and extending from the actuator side to the housing side. The actuator side and the housing side are separated by an offset thickness, and the opening and the offset thickness at least partially define a resonant cavity for the piezoelectric speaker.

An electronic assembly for a medical device is also provided. The electronic assembly includes: a carrier substrate; a piezoelectric speaker having a first major side and a second major side, the first major side coupled to the carrier substrate; and an offset ring coupled to the second major side of the piezoelectric speaker. The offset ring has an opening formed therein through which a portion of the second major side is exposed. The opening at least partially defines a resonant cavity for the piezoelectric speaker.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 36 is a side view of a belt clip suitable for use with the fluid infusion device; and FIG. 37 is an exploded perspective view of the belt clip shown in FIG. 36.

DETAILED DESCRIPTION

Figure 1:
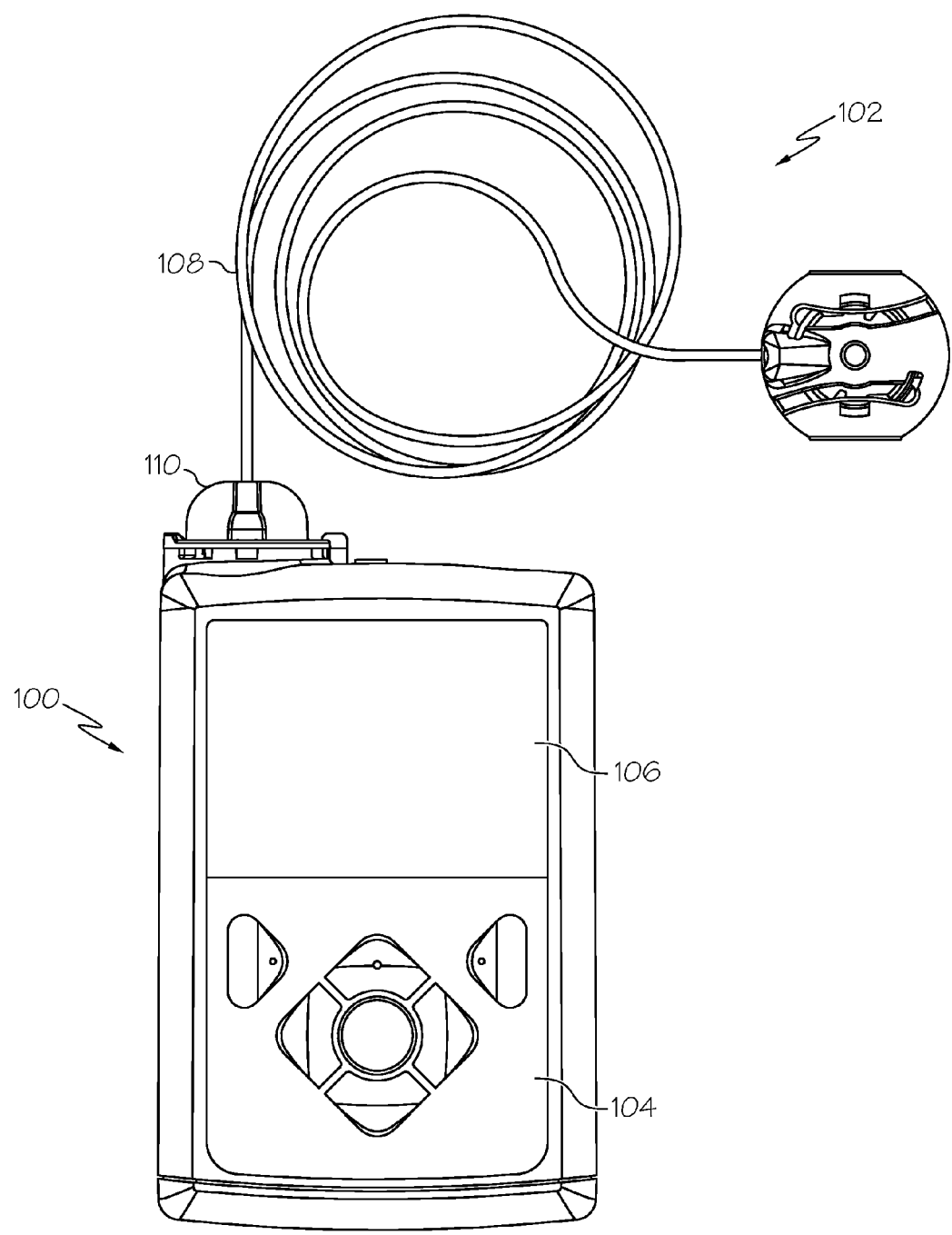
FIG. 1 is a schematic representation of an embodiment of a fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard," and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

For or the sake of brevity, conventional features and characteristics related to infusion system operation, insulin pump and/or infusion set operation, blood glucose sensing and monitoring, force sensors, signal processing, and other functional aspects of an infusion device (and the individual operating components of the infusion device) may not be described in detail here. Examples of infusion pumps and/or related pump drive systems used to administer insulin and other medications may be of the type described in, but not limited to, U.S. Pat. Nos.: 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

The subject matter described here relates to various features, components, assembly methodologies, and technology associated with a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

Figure 2:
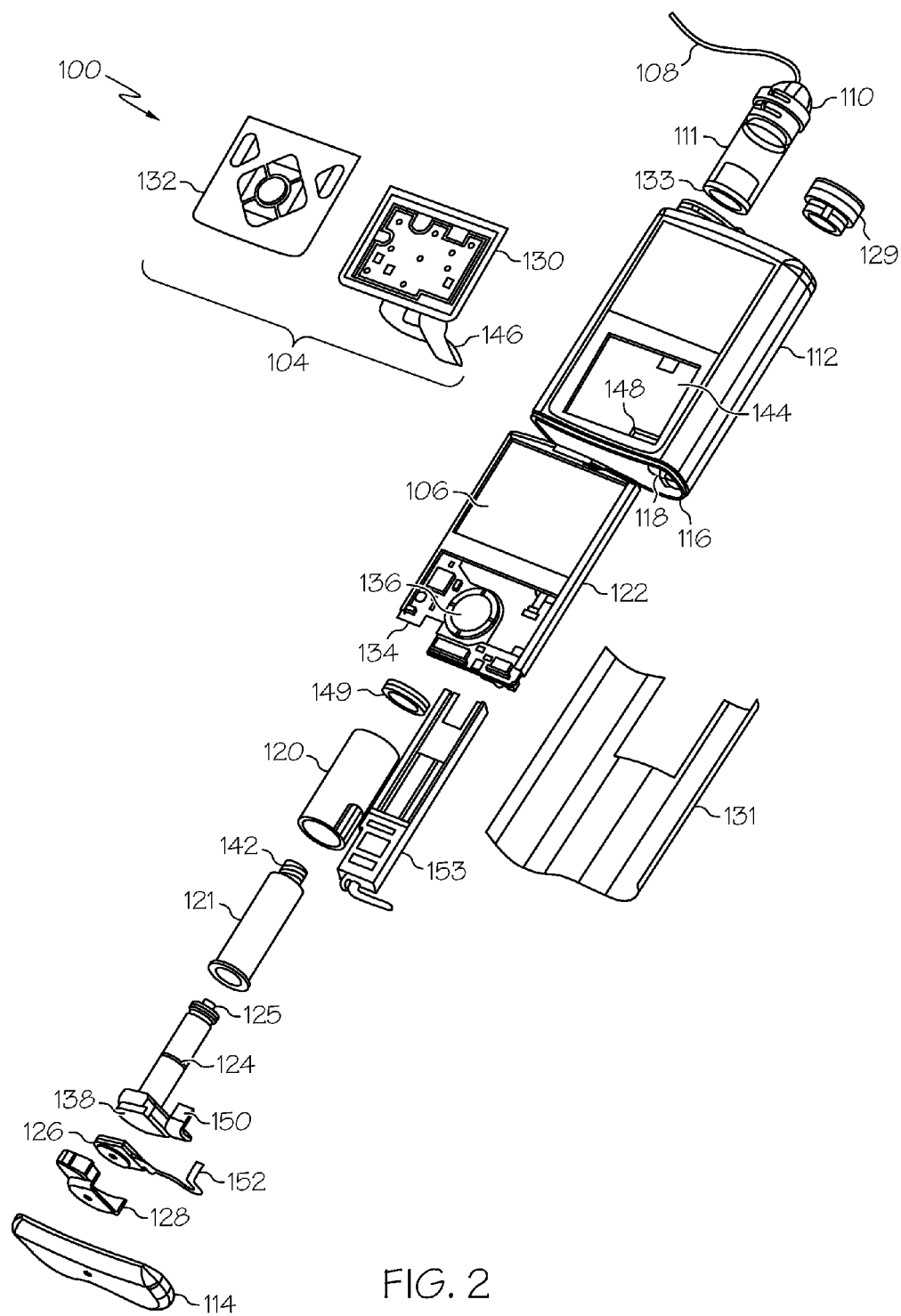
FIG. 2 is an exploded perspective view of the fluid infusion device.

FIG. 1 is a schematic representation of an embodiment of a fluid infusion device 100, and FIG. 2 is an exploded perspective view of the fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of conventional and well known fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

Referring to FIG. 1, the fluid infusion device 100 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; etc. In some embodiments, the display element 106 is realized as a touch screen display element and, therefore, the display element 106 also serves as a user interface component.

The fluid infusion device 100 accommodates a fluid reservoir (hidden from view in FIG. 1) for the fluid to be delivered to the user. A length of tubing 108 fluidly couples the fluid reservoir to the infusion set 102. The tubing 108 extends from the fluid infusion device 100 to the infusion set 102, which provides fluid communication with the body of the user. A removable cap or fitting 110 is suitably sized and configured to accommodate replacement of fluid reservoirs (which are typically disposable) as needed. In this regard, the fitting 110 is designed to accommodate the fluid path from the fluid reservoir to the tubing 108.

For the sake of brevity, FIG. 2 is a simplified depiction of the fluid infusion device 100, which does not include all of the elements, components, and features that would otherwise be present in a typical embodiment. It should be appreciated that a deployed implementation of the fluid infusion device 100 will include additional features, components, and elements that are not shown in the figures. FIG. 2 also depicts an exemplary fluid reservoir 111 that can be installed into the fluid infusion device 100.

The embodiment of the fluid infusion device 100 illustrated in FIG. 2 includes a housing 112 and a housing end cap 114 that is coupled to an end 116 of the housing 112 to enclose components within the housing 112. These internal components include, without limitation: a battery tube subassembly 118; a sleeve 120; a slide 121; an electronics assembly 122; a drive motor assembly 124 having a drive screw 125; a force sensor 126; and a motor support cap 128. FIG. 2 also depicts some components that are located outside the housing 112, namely, a battery cap 129, a keypad assembly 130, a back cover 131, and a graphic keypad overlay 132 for the keypad assembly 130. The keypad assembly 130 and the graphic keypad overlay 132 may be considered to be part of the user interface 104 of the fluid infusion device 100.

The battery tube subassembly 118 accommodates a battery or battery pack, which serves as the primary power supply for the electronics module, infusion pump hardware, and other electronic components of the fluid infusion device 100. As shown in FIG. 2, the battery tube subassembly 118 is positioned at one side of the housing 112 (to provide clearance and space for the remaining internal components). A detailed description of the battery tube subassembly 118 appears below in a separate section of this specification.

When the fluid infusion device 100 is assembled, the sleeve 120 is positioned at the side of the housing 112 opposite the battery tube subassembly 118. The sleeve 120 serves as a keying feature to prevent the slide 121 from rotating when the drive screw 125 of the drive motor assembly 124 rotates. The sleeve 120 receives the slide 121, which has internal threads for assembly onto the drive screw 125. Thus, rotation of the drive screw 125 causes the slide 121 to extend or retract relative to the drive motor assembly 124. When the fluid infusion device is assembled and operational, the slide 121 contacts a plunger 133 to engage the fluid reservoir 111 and control delivery of fluid from the fluid infusion device 100.

The electronics assembly 122 includes a carrier substrate 134, such as a printed circuit board or other structure, upon which various electronic and other components are mounted. In this regard, the electronics assembly 122 may include a suitably configured electronics module, which may include or cooperate with a power supply, at least one memory element, at least one processor, processing logic, and device software, firmware, and application programs. Moreover, the illustrated embodiment of the electronics assembly 122 includes a piezoelectric speaker 136 that is coupled to the carrier substrate 134. A detailed description of the piezoelectric speaker 136 appears below in a separate section of this specification.

The fluid infusion device 100 cooperates with a fluid reservoir 111, which is actuated to deliver measured doses of fluid to the user via the infusion set 102 (see FIG. 1). While certain embodiments accommodate disposable, prefilled reservoirs, alternative embodiments may use refillable cartridges, syringes or the like. A cartridge can be prefilled with insulin (or other drug or fluid) and inserted into the housing 112. Alternatively, a cartridge could be filled by the user using an appropriate adapter and/or any suitable refilling device.

When the fluid infusion device 100 is assembled, the drive motor assembly 124 is located in the housing 112 and is covered by the housing end cap 114. The force sensor 126 is positioned below the drive motor assembly 124, and the force sensor 126 is covered by the motor support cap 128, which in turn is covered by the housing end cap 114. A detailed description of the motor support cap 128 appears below in a separate section of this specification.

In one implementation, the force sensor 126 is affixed to the base end 138 of the drive motor assembly 124 such that the force sensor 126 reacts when the combination of the drive motor assembly 124 and the force sensor 126 bears against the motor support cap 128. In another implementation, the force sensor 126 is affixed to the motor support cap 128 such that the force sensor 126 reacts when the drive motor assembly 124 bears against the force sensor 126. The configuration and arrangement of the drive motor assembly 124 and the force sensor 126 allows the force sensor 126 to react to forces imparted thereto by the drive motor assembly 124 and/or forces imparted to the drive motor assembly 124 via the fluid pressure of the fluid reservoir.

The drive motor assembly 124 includes an electric motor that is actuated and controlled by the electronics module of the fluid infusion device 100. The motor is preferably realized as a brushless DC motor that rotates in a stepwise or discrete manner corresponding to the desired number of fluid delivery strokes. Alternatively, the motor could be a DC motor, a solenoid, or the like. The motor may optionally include an encoder, which cooperates with the electronics module of the fluid infusion device 100 to monitor the number of motor rotations or portions thereof. This in turn can be used to accurately determine the position of the slide 121, thus providing information relating to the amount of fluid dispensed from the fluid reservoir, which is actuated by movement of the slide 121.

The illustrated embodiment of the slide 121 includes a coupler 142, which may be attached to or integrated with the slide 121, as depicted in FIG. 2. The slide 121 is sized to fit within the housing of the fluid reservoir 111, which enables the slide 121 to operatively cooperate with the fluid reservoir 111. In this regard, the slide 121 serves as a linear actuation member for the fluid reservoir 111. The fluid reservoir 111 includes a plunger 133 or piston with at least one sealing element or feature (e.g., one or more O-rings, integral raised ridges, or a washer) for forming a fluid and air tight seal with the inner wall of the fluid reservoir 111. As mentioned previously, the fluid reservoir 111 is secured into the housing 112 with the fitting 110, which also serves as the interface between the fluid reservoir 111 and the infusion set tubing 108 (see also FIG. 1). For this embodiment, the piston of the fluid reservoir 111 is connected to the slide 121 by a releasable coupling mechanism or feature. For example, the piston may have a female portion that receives the coupler 142. The female portion is positioned at the end face of the piston, and it could include a threaded cavity that engages threads of the coupler 142.

During operation of the fluid infusion device 100, rotation of the drive shaft of the drive motor assembly 124 rotates the drive screw 125, which in turn moves the slide 121, relative to the base end 138 of the drive motor assembly 124. Thus, rotation of the drive shaft results in axial displacement of the slide 121 and, therefore, axial displacement of the coupler 142. Such displacement of the coupler 142 moves the piston of the fluid reservoir 111 to deliver a predetermined or commanded amount of medication or liquid from the fluid infusion device 100. As described above, if a stepper motor is employed, then the drive motor assembly 124 can regulate delivery of fluid from the fluid infusion device 100 in discrete actuation or delivery strokes. In some embodiments, the drive shaft of the drive motor assembly 124 and the slide 121 are coaxially centered within the longitudinal axis of travel of the piston. In certain alternative embodiments, one or more of these components may be offset from the center of the axis of travel.

As mentioned above, certain embodiments of the fluid infusion device 100 accommodate removable and replaceable fluid reservoirs. When the slide 121 (and, therefore, the piston of the fluid reservoir 111) is in its fully extended position, the piston has forced most, if not all, of the fluid out of the fluid reservoir 111. After the piston has reached the end of its travel path, indicating that the fluid reservoir 111 has been depleted, the fluid reservoir 111 may be removed by disengaging the plunger 133 from the coupler 142 of the slide 121. After the empty (or otherwise used) fluid reservoir 111 is removed, the electronics module or control system of the fluid infusion device 100 initiates a rewind operation during which the motor rotates in the reverse direction to rewind the slide 121 back to its fully retracted position. Thereafter, a new or refilled fluid reservoir can be installed, seated, and primed for use. In operation, the force sensor 126 may be used to determine when the slide 121 contacts the piston, when the coupler 142 is properly seated in the female portion of the piston, when the fluid reservoir 111 has been primed and is ready to deliver measured doses of fluid, when an occlusion is present in the fluid flow path, and/or when the fluid infusion device 100 has been subjected to shock or impact.

The keypad assembly 130 is coupled to a keypad mounting area 144 of the housing 112, and the graphic keypad overlay 132 overlies the keypad assembly 130. The keypad assembly 130 includes features corresponding to keys, buttons, switches, or other user interface items, and the graphic keypad overlay 132 may include visual indicia associated with the actuation elements of the keypad assembly 130, decorative graphics, alphanumeric labeling, etc. A detailed description of the keypad assembly 130 and the graphic keypad overlay 132 appears below in a separate section of this specification.

The fluid infusion device 100 may be manufactured and assembled in the manner summarized below, and using the techniques, technology, and approaches described in more detail in the separate sections of this specification. The following description of an exemplary assembly approach is not intended to be limiting or exhaustive and, indeed, alternative fabrication and assembly techniques could be utilized to produce the fluid infusion device 100. Moreover, it may be possible or desirable to reorder some of the assembly steps described below, depending upon the particular circumstances and capabilities of the manufacturing facility.

For this example, the battery tube subassembly 118 is assembled (see FIG. 3) so that it can be integrally molded into the housing 112. In this regard, the housing 112 is preferably realized as a molded hard plastic shell, which provides a strong, stiff, and rigid protective case for the internal components of the fluid infusion device 100. The keypad assembly 130 can then be bonded to the keypad mounting area 144. The keypad assembly 130 can be installed by feeding its flex circuit tail 146 through a corresponding slot 148 in the housing 112. As described in more detail below, a sealing element (not separately shown in FIG. 2) may be installed overlying the keypad assembly 130 to form a fluid resistant seal with the housing 112. Next, the pre-assembled electronics assembly 122 is inserted into the housing 112 while keeping the flex circuit tail 146 of the keypad assembly 130 clear. The force sensor 126 is then bonded to the base end 138 of the drive motor assembly 124, and the slide 121 is installed onto the drive screw 125. Accordingly, the drive motor assembly 124 and the force sensor 126 together form a subassembly that is later installed into the housing 112. Thereafter, the sleeve 120 is inserted over the slide 121 and keyed in place. A slide seal 149 is installed onto the slide 121 and bottomed out against the sleeve 120. The subassembly (including the drive motor assembly 124, the attached force sensor 126, the slide 121, and the sleeve 120) is then inserted into the housing 112.

Electrical connections are then established from the drive motor assembly 124, the force sensor 126, and the keypad assembly 130 to the electronics assembly 122 using suitable conductors, e.g., the flex circuit tail 146, flex cables, wires, or the like. For example, contacts on the battery tube subassembly 118 are connected to corresponding contact points or conductors on the electronics subassembly 122. As shown in FIG. 2, the drive motor assembly 124 has an electrical lead 150, and the force sensor 126 has an electrical lead 152. These electrical leads 150, 152, along with the flex circuit tail 146 of the keypad assembly 130, are connected (directly or indirectly) to appropriate points, receptacles, or conductors on the electronics assembly 122. In addition, electrical connections are established for a rechargeable battery and a vibrator motor (not shown).

Next, an assembly shim 153 is inserted into the housing 112 to bias the electronics subassembly 122 towards a display window of the housing 112 and to "lock" the internal components in place. As described in more detail below, the assembly shim 153 also holds certain leads, flex circuit elements, and/or wires in place for ease of assembly. Thereafter, the motor support cap 128 is installed over the force sensor 126 and the base end 138 of the drive motor assembly 124, and secured to the interior surface of the housing 112 (as described in more detail below). A dampener element (not shown) is installed onto the housing end cap 114, which is then attached to the end 116 of the housing 112 to enclose the internal components within the housing 112. In practice, the housing end cap 114 can be ultrasonically welded to the housing 112. The graphic keypad overlay 132 is then adhered to the keypad assembly 130 (and/or to the sealing element).

The fluid infusion device 100 employs a number of features, components, and elements that enhance its performance, user-friendliness, manufacturability, robustness, and the like. For ease of description, some of these features, components, and elements will be presented below under their respective section headings. In practice, the fluid infusion device 100 could implement some or all of the features, components, and elements described below.

Battery Tube Subassembly

Figure 3:
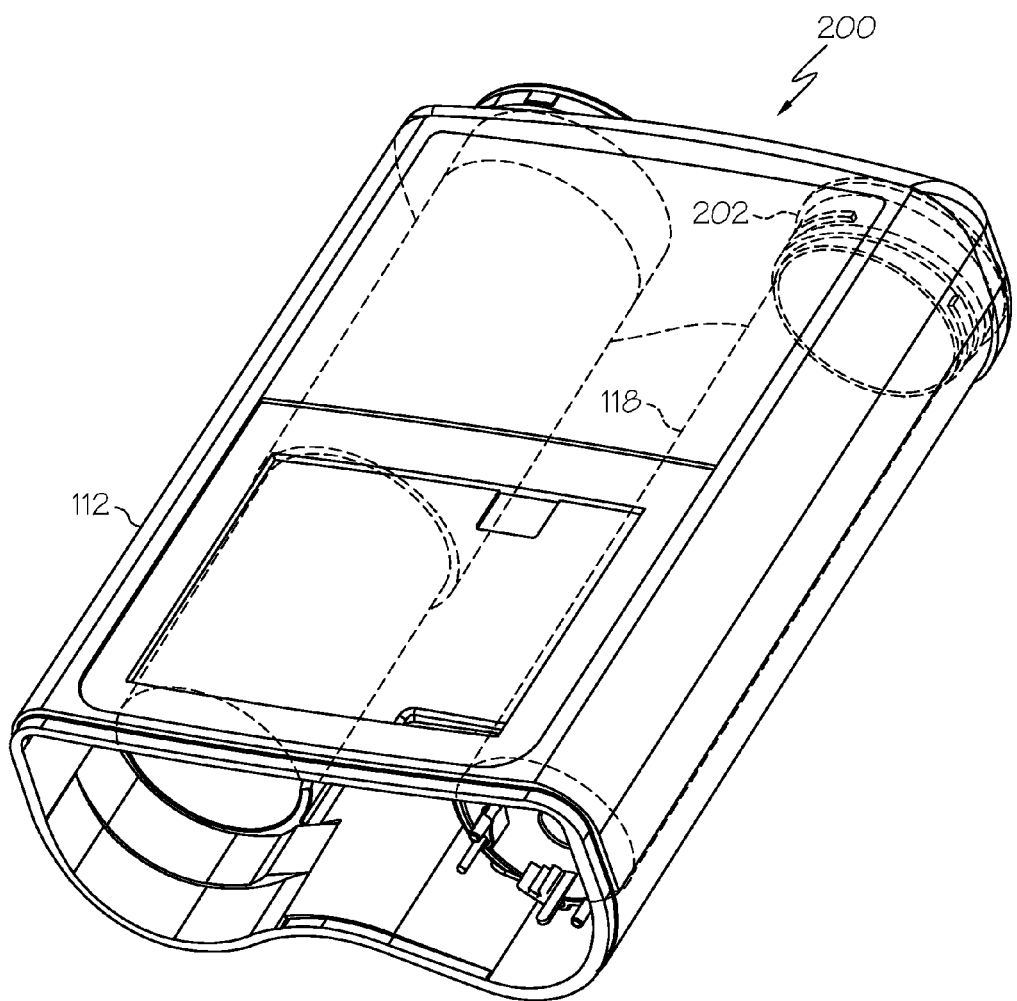
FIG. 3 is a perspective phantom view of the housing of the fluid infusion device.

As mentioned above with reference to FIG. 2, the fluid infusion device 100 includes a battery tube subassembly 118 located inside the housing 112. FIG. 3 is a perspective phantom view of the housing 112; the battery tube subassembly 118 is shown in its installed position inside the housing 112. The battery tube subassembly 118 is accessible from the top end 200 of the housing 112, via a cap or fitting 202. The fitting 202 allows the user to remove and replace the battery or battery pack as needed. In practice, the fitting 202 is fluid resistant to inhibit the incursion of fluid (e.g., water) and contaminants into the battery tube subassembly 118.

Figure 4:
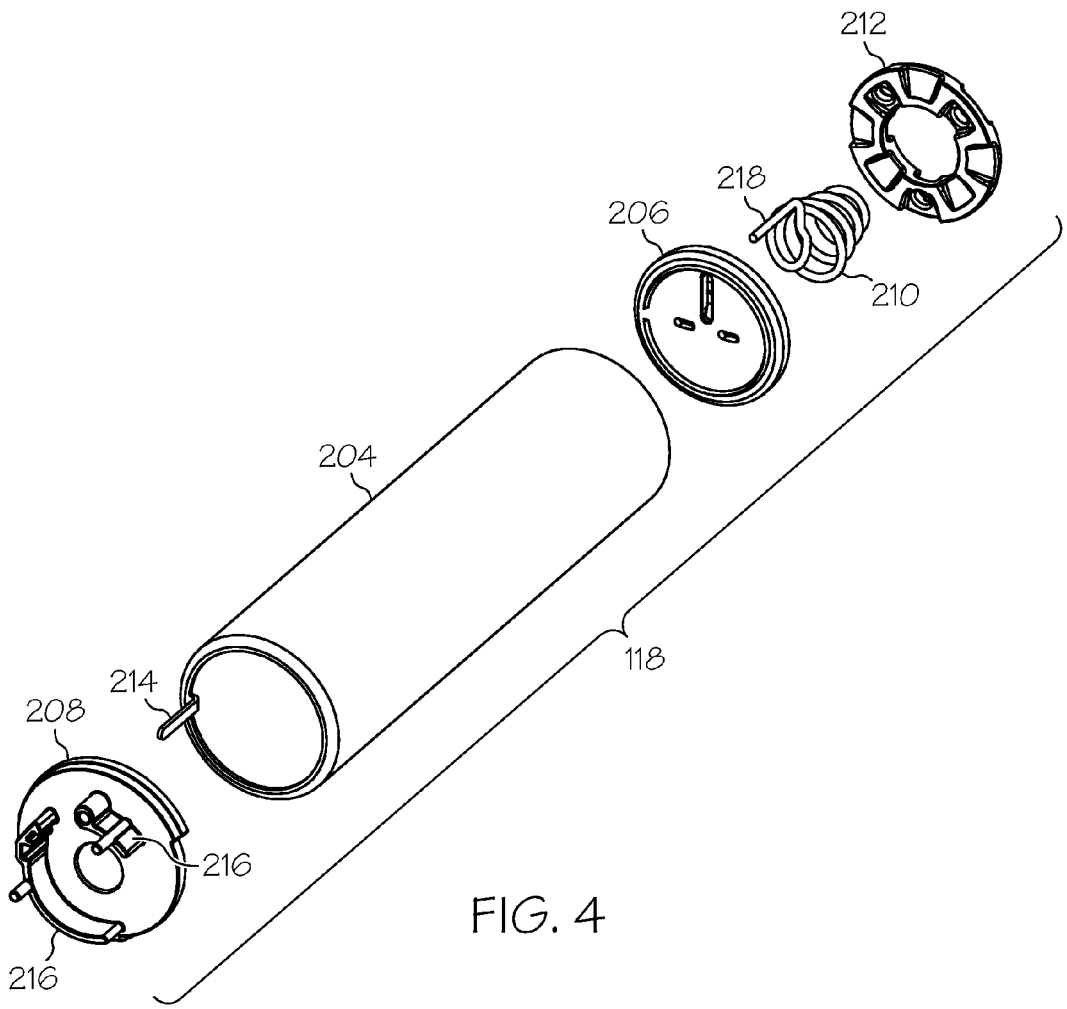
FIG. 4 is an exploded perspective view of a battery tube subassembly suitable for use with the fluid infusion device.
Figure 5:
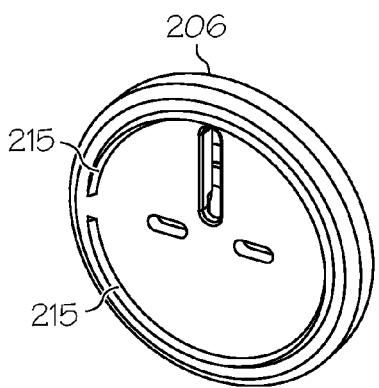
FIG. 5 is a perspective view of a spring support disk of the battery tube subassembly.
Figure 6:
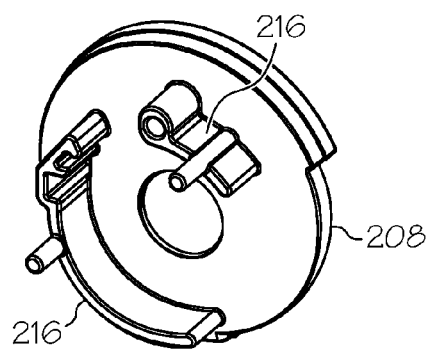
FIG. 6 is a perspective view of a vibration motor support disk of the battery tube subassembly.

FIG. 4 is an exploded perspective view of the battery tube subassembly 118. This particular embodiment of the battery tube subassembly 118 includes, without limitation: a battery sleeve 204; a spring support disk 206; a vibration motor support disk 208; a spring 210 (or other suitable electrical contact); and a shock absorbing element 212. FIG. 5 is a perspective view of the spring support disk 206, and FIG. 6 is a perspective view of the vibration motor support disk 208. A detailed description of the shock absorbing element 212 appears below in a separate section of this specification.

The battery tube subassembly 118 is suitably configured so that it can be molded into the housing 112 (see FIG. 3). This reduces part count in the final assembly and creates a permanent bond between the battery sleeve 204 and the housing 112. Moreover, the battery sleeve 204 becomes part of the housing 112, thus eliminating a leak path, adding strength, reducing assembly steps, and reducing cost.

In certain implementations, the battery sleeve 204 is drawn and formed to size from stainless steel with a tang 214 extending from the rolled end. The tang 214 is the positive contact that is soldered to the power board at the next higher assembly level. The rolled end is used to capture the spring support disk 206, which forms the bottom end cap of the battery compartment defined inside the battery sleeve 204. In practice, the battery sleeve 204 is shaped and sized to accommodate the dimensions of the battery or battery pack, e.g., a AA battery.

For this embodiment, the spring support disk 206 is molded from polycarbonate or a similar material. The spring support disk 206 becomes the inside component at the end of the battery sleeve 204. The spring support disk 206 supports the spring 210 and provides features to capture the spring 210 and hold it in position. An energy director ring 215 is provided on the spring support disk 206. The energy director ring 215 is designed to facilitate welding of the spring support disk 206 to the vibration motor support disk 208, thereby pinching the rolled end of the battery sleeve 204 between the spring support disk 206 and the vibration motor support disk 208 and creating a solid bottom to the battery sleeve 204.

The vibration motor support disk 208 may also be molded from polycarbonate. The vibration motor support disk 208 becomes the external component at the end of the battery sleeve 204. The vibration motor support disk 208 has a through hole for the spring 210 and the tang 214 of the battery sleeve 204. The vibration motor support disk 208 is welded to the spring support disk 206 and, therefore, forms the bottom of the battery sleeve 204. The vibration motor support disk 208 is designed to fit the vibration motor. In this regard, the vibration motor support disk 208 has two walls 216 that allow the vibration motor to be bonded to the vibration motor support disk 208 at the next assembly level. An ultraviolet cure adhesive is used to bond the vibration motor (not shown) to the vibration motor support disk 208 in the final assembly.

The spring 210 represents the negative electrical contact for the battery or battery pack. In certain embodiments, the spring 210 is coiled from beryllium copper wire (or other electrically conductive metal) for strength and low electrical resistance. The spring 210 has an end leg 218 that passes through both the spring support disk 206 and the vibration motor support disk 208. The spring 210 is held in place on the spring support disk 206 with features that snugly fit inside the last coil. The end leg 218 of the spring 210 passes through the vibration motor support disk 208 and it is soldered to the power board as the negative contact.

The components of the battery tube subassembly 118 can be assembled as follows. The spring 210 is located on the spring support disk 206, which is then inserted into the battery sleeve 204 and against the rolled edge. The vibration motor support disk 208 is then placed against the spring support disk 206 and the outside rolled edge of the battery sleeve 204, and then welded together using an ultrasonic welder. This creates the bottom or base end for the battery sleeve 204. That assembly is then placed on the core of the molding machine and inserted into the mold. The housing 112 is then molded over the battery tube subassembly 118 to create a very clean one-piece housing with an integrated battery compartment or receptacle. The shock absorbing element 212 can be installed into the battery sleeve 204 and around the spring 210 after completion of the molding process.

Shock Absorbing Element

Figure 7:
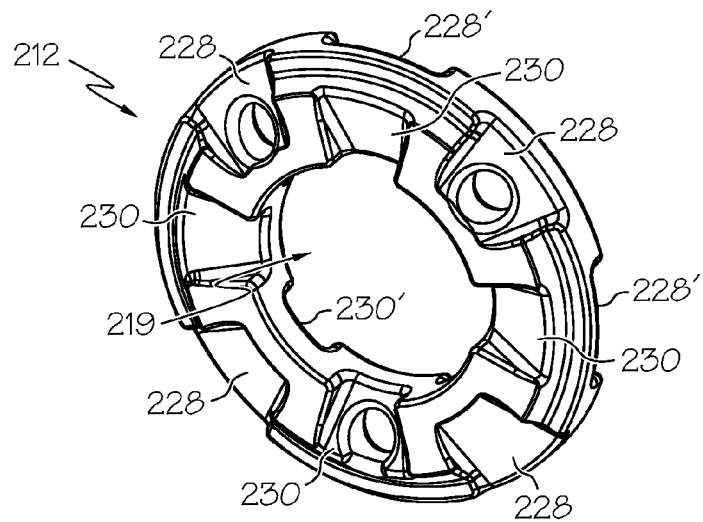
FIG. 7 is a perspective view of a shock absorbing element suitable for use within the battery tube subassembly of the fluid infusion device.
Figure 8:
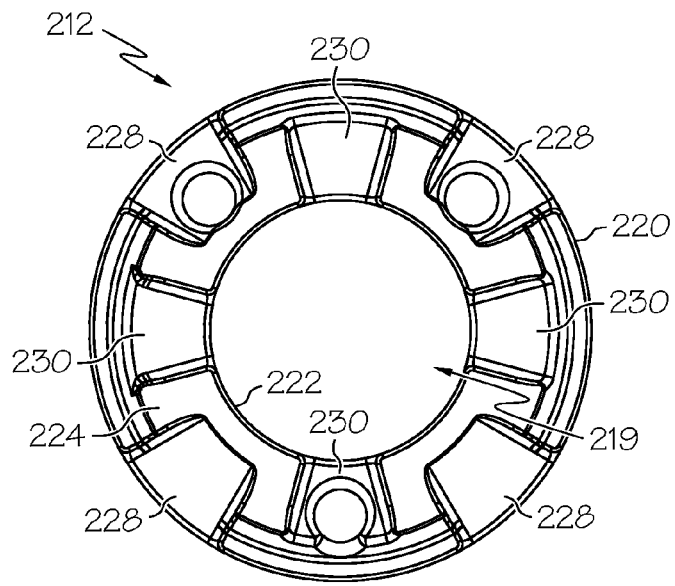
FIG. 8 is a top view of the shock absorbing element.
Figure 9:
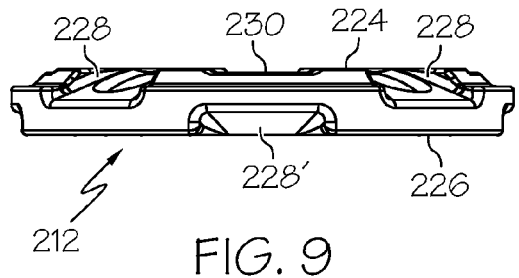
FIG. 9 is a side view of the shock absorbing element.
Figure 10:
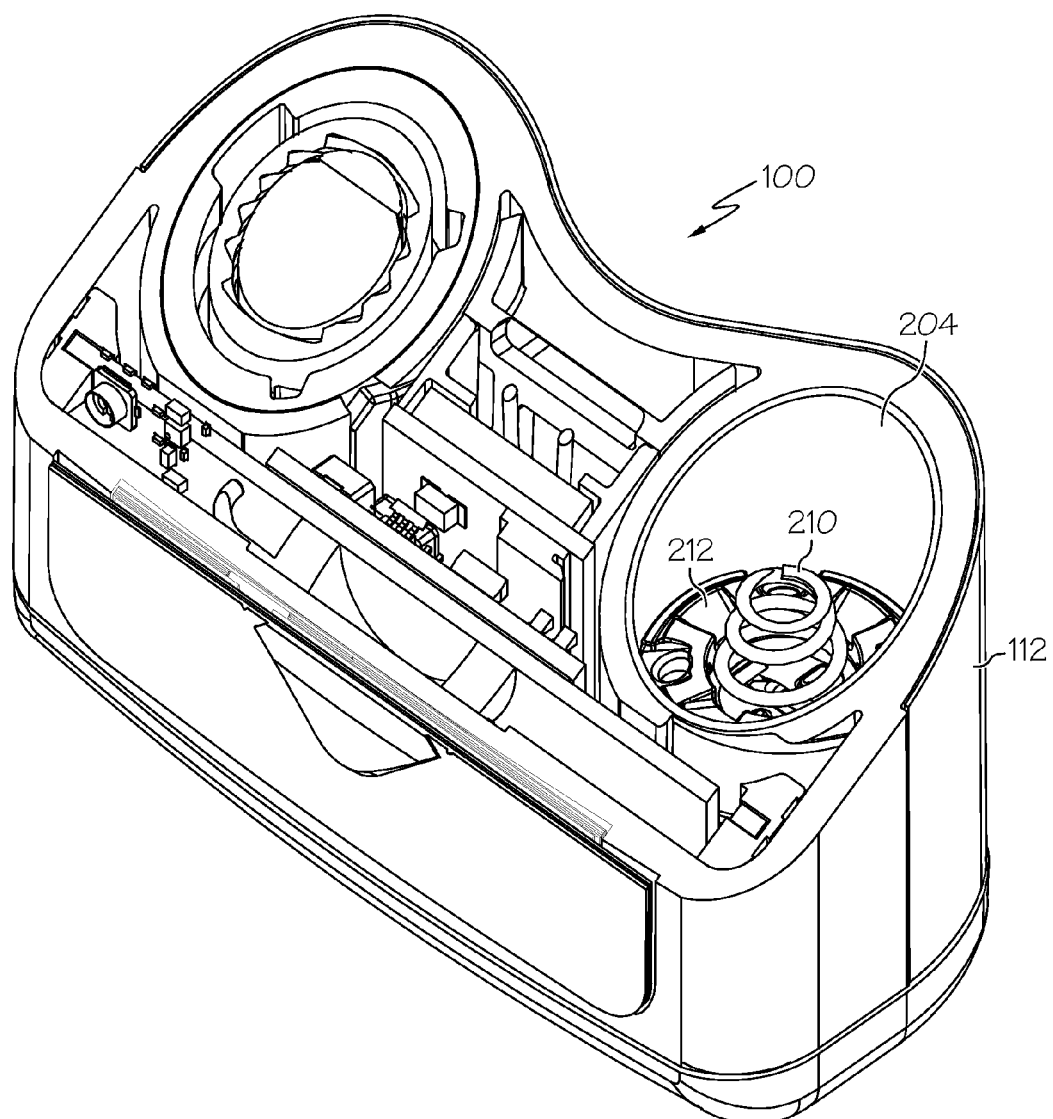
FIG. 10 is a perspective cross sectional view of a portion of the fluid infusion device, depicting the shock absorbing element installed in a battery sleeve.

As mentioned in the preceding section, the shock absorbing element 212 is installed inside the battery tube subassembly 118, which serves as the battery receptacle for the fluid infusion device 100. FIG. 7 is a perspective view of the shock absorbing element 212, FIG. 8 is a top view of the shock absorbing element 212, FIG. 9 is a side view of the shock absorbing element 212, and FIG. 10 is a perspective cross sectional view of a portion of the fluid infusion device 100 (FIG. 10 depicts the shock absorbing element 212 as installed). For this embodiment, the bottom view of the shock absorbing element 212 is similar or identical to its top view.

The illustrated embodiment of the shock absorbing element 212 is ring-shaped, and it surrounds the spring 210 (see FIG. 10). In other words, when the shock absorbing element 212 installed properly near the base end of the battery sleeve 204, the spring 210 protrudes through the shock absorbing element 212. Referring again to FIG. 4, the base end of the battery sleeve 204 corresponds to the top surface of the spring support disk 206 in this embodiment. Consequently, after the battery is inserted into the battery sleeve 204, the shock absorbing element 212 will reside between the base end of the battery sleeve 204 and the battery.

The shock absorbing element 212 is designed to absorb the shock from the battery (e.g., a AA sized battery) or battery pack housed inside the battery sleeve 204. The shock absorbing element 212 is placed at the bottom of the battery sleeve 204, and attached to the base end using, for example, an adhesive. As shown in FIG. 10, the shock absorbing element 212 is located around the spring 210, which resides within the battery sleeve 204 near the base end. This configuration protects the spring 210 against over compression by stopping the battery above the compressed "solid" height of the spring 210, which could cause damage to the fluid infusion device 100. In certain embodiments, the shock absorbing element 212 is compression molded and composed of a resilient electrical insulator material, such as rubber, polyurethane, plastic, or the like, which has properties that increase its shock absorbing characteristics. Thus, the shock absorbing element 212 is preferably formed as a one-piece component composed of the chosen resilient material. Moreover, the shape of the shock absorbing element 212 is suitably designed with various shock absorbing features integrally formed therein; these integral features improve the ability of the shock absorbing element 212 to absorb loads and dissipate kinetic energy that might be associated with motion of the battery toward the base end. In practice, the shock absorbing element 212 reduces shock loads transmitted from the battery to the housing 112.

Referring to FIGS. 7-9, the shock absorbing element 212 has a through hole 219 formed therein, an outer perimeter 220 (which corresponds to the outer circumference when the perimeter is circular), and an inner circumference 222 that is defined by the edge of the through hole 219. The outer perimeter 220 is sized and shaped to accommodate placement of the shock absorbing element 212 in the battery sleeve 204. In this regard, the outer perimeter 220 could be sized for a press fit in the battery sleeve 204 or, in the alternative, to provide some clearance between the shock absorbing element 212 and the inner wall of the battery sleeve 204. Some amount of clearance may be desirable to allow the shock absorbing element to compress, expand, and deform in response to forces imparted thereto.

The through hole 219 is sized and shaped to accommodate the spring 210, as depicted in FIG. 10. For this particular embodiment, the through hole 219 is generally round or circular when viewed from the top or bottom, as shown in FIG. 8. Moreover, the outer perimeter 220 and the through hole 219 are coaxial in the illustrated ring-shaped embodiment.

The shock absorbing element 212 has a top side 224 (which faces the battery) and a bottom side 226 (which faces the base end of the battery sleeve 204)—FIG. 8 shows the top side 224. Notably, the shock absorbing element 212 has at least one shock absorbing feature integrally formed on its top side 224 and/or at least one shock absorbing feature formed on its bottom side 226, and these shock absorbing features are designed to dissipate kinetic energy associated with motion of the battery relative to the battery sleeve 204. Depending upon the particular embodiment, a shock absorbing feature may be, without limitation: a radial ridge formed from the resilient material; a radial depression formed in the resilient material; an angled or tilted outer depression formed in the resilient material; an angled or tilted inner depression formed in the resilient material; a rib; a protrusion; a hole; texture; a rim; or the like.

The illustrated embodiment of the shock absorbing element 212 employs an alternating pattern of angled depressions on each side. More specifically, the top side 224 has a plurality of angled outer depressions 228 interlaced with a plurality of angled inner depressions 230. Each of the angled outer depressions 228 has a high edge located near or terminating at the through hole 219, and a low edge located near or terminating at the outer perimeter 220. Thus, the angled outer depressions 228 are downwardly sloped toward the outer perimeter (see the side view of FIG. 9). In contrast, each of the angled inner depressions 230 has a high edge located near or terminating at the outer perimeter, and a low edge located near or terminating at the through hole 219. Accordingly, the angled inner depressions 230 are downwardly sloped toward the through hole 219 (see FIG. 7).

In certain embodiments, at least one angled outer depression is formed on each side of the shock absorbing element 212, and at least one angled inner depression is formed on each side of the shock absorbing element 212. For this example, the bottom side 226 of the shock absorbing element 212 may also have four angled outer depressions and four angled inner depressions formed therein, and the depressions may be arranged in an alternating manner. Moreover, each angled outer depression formed on the top side 224 is aligned with a respective angled inner depression formed on the bottom side 226, and each angled outer depression formed on the bottom side 226 is aligned with a respective angled inner depression formed on the top side 224. This aligned relationship is shown in FIG. 7 and FIG. 9, where depressions formed in the bottom side 226 are identified using prime notation. Thus, the angled inner depressions 230 on the top side 224 are aligned with the angled outer depressions 228' on the bottom side 226, and the angled outer depressions 228 on the top side 224 are aligned with the angled inner depressions 230' on the bottom side 226.

The depressions formed in the shock absorbing element 212 are radially oriented in that they resemble longitudinal channels that run in the radial direction. Note that the configuration of the depressions also forms a number of radial ridges in the resilient material. These radial ridges are located between the depressions on each side of the shock absorbing element 212. The depressions, radial ridges, and other features of the shock absorbing element 212 contribute to its compressive, rebound, and energy absorbing characteristics.

Piezoelectric Speaker Offset Element

Figure 11:
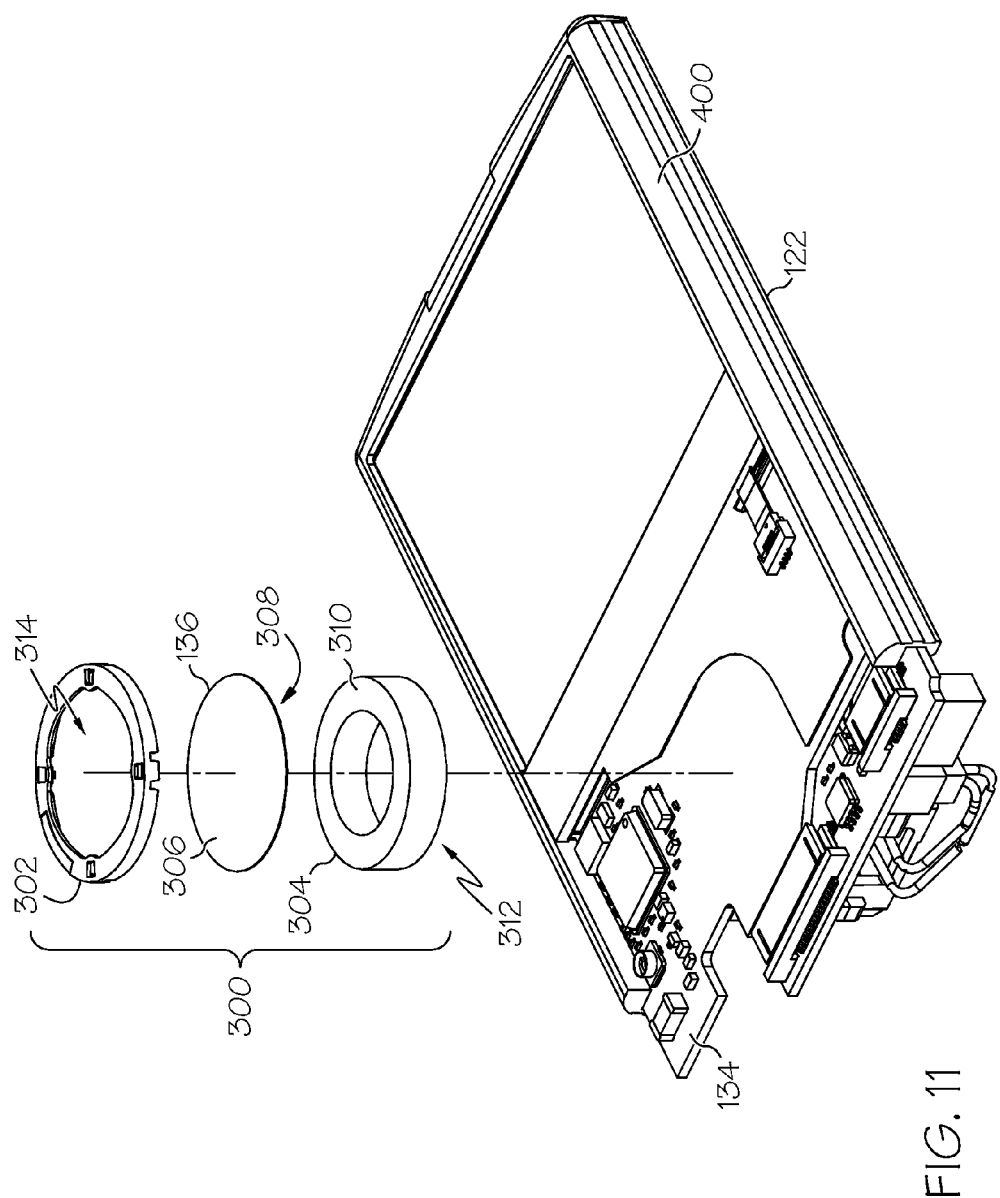
FIG. 11 is an exploded perspective view of an electronics assembly suitable for use with the fluid infusion device.

As mentioned above with reference to FIG. 2, the electronics assembly 122 of the fluid infusion device 100 might include at least one piezoelectric speaker 136 on the carrier substrate 134. FIG. 11 is a perspective view of the electronics assembly 122, with a transducer assembly 300 shown in exploded form. The illustrated embodiment of the transducer assembly 300 includes the piezoelectric speaker 136, an offset element 302, and a mounting component 304.

In a conventional piezoelectric speaker mounting environment, the piezoelectric speaker is mounted directly to a surface, such as the interior surface of the case or housing of the device. This typically works for systems that have through holes in the case or housing (through which sound generated by the speaker is emitted). The fluid infusion device 100, however, employs a fluid resistant housing 112 that does not contain any sound-transmitting holes.

The piezoelectric speaker 136 functions by vibrating to produce sounds. If the piezoelectric speaker 136 is mounted directly to a relatively rigid housing (such as hard plastic), the piezoelectric speaker cannot efficiently and effectively vibrate the housing.

Thus, the speaker does not efficiently produce sounds. To address this shortcoming of traditional designs, the transducer assembly 300 employs the offset element 302, which creates a gap between the actuator of the piezoelectric speaker 136 and the rigid plastic of the housing 112. The gap allows the piezoelectric speaker 136 to easily vibrate the air between the inner surface of the housing 112 and the surface of the piezoelectric speaker 136. When the resonant frequency of the system is reached, the air vibrates violently and the vibrations are transmitted to the rigid plastic of the housing 112. The magnitude of the vibrations is generally much higher relative to an arrangement where the piezoelectric speaker is mounted directly to a housing.

Referring to FIG. 11, the transducer assembly 300 is coupled to the carrier substrate 134 by way of the mounting component 304. In this regard, the illustrated embodiment of the piezoelectric speaker 136 is realized as a flat disk having a top major side 306 and a bottom major side 308. The bottom major side 308 is attached to the upper surface 310 of the mounting component 304, and the lower surface 312 of the mounting component is attached to the carrier substrate 134. In practice, pressure sensitive adhesive can be used to affix the mounting component 304 to the carrier substrate 134, and to affix the piezoelectric speaker 136 to the mounting component 304. Although not depicted in the figures, appropriate electrical connections are established between the piezoelectric speaker 136 and corresponding contact points formed on the carrier substrate 134, as is well understood by those familiar with electric transducers. For example, conductive wires, ribbons, or traces may be routed from the piezoelectric speaker 136, through the center of the mounting component 304, and to carrier substrate 134. Alternatively, conductive wires, ribbons, or traces could be routed between the upper surface 310 of the mounting component 304 and the bottom major side 308 of the piezoelectric speaker 136.

In certain embodiments, the mounting component 304 is a ring-shaped element formed from a resilient material such as rubber, foam, polyurethane, or the like. The resiliency of the mounting component 304 results in biasing of the piezoelectric speaker 136 away from the carrier substrate 134 in the absence of other external forces. Thus, force applied to the top of the piezoelectric speaker 136 and/or to the top of the offset element 302 will compress the mounting component 304. Removal of the applied force, however, will allow the mounting component 304 to decompress and spring back into its nominal shape and configuration. The resilient nature of the mounting component 304 allows it to bias the offset element 302 against the interior surface of the housing 112 (as explained below).

The top major side 306 of the piezoelectric speaker 136 is coupled to the offset element 302. For this particular embodiment, the offset element 302 is coupled to the piezoelectric speaker 136 by way of a snap fit or press fit engagement. In this regard, clips or tab features (see FIG. 13) can be used to secure the piezoelectric speaker 136 to the offset element 302. The offset element 302 (which is ring-shaped in this embodiment) has an opening 314 formed therein, through which a portion of the top major side 306 is exposed (see FIG. 2). As explained in more detail below, the opening 314 at least partially defines a resonant cavity for the piezoelectric speaker 136.

Figure 12:
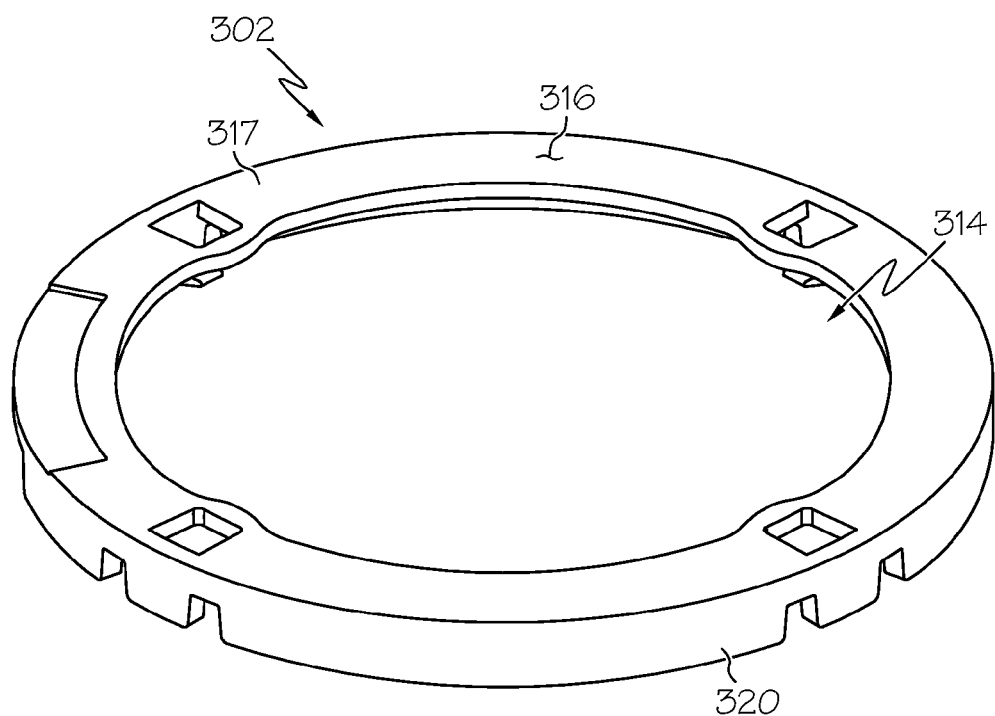
FIG. 12 is a top perspective view of an offset element for a piezoelectric speaker.
Figure 13:
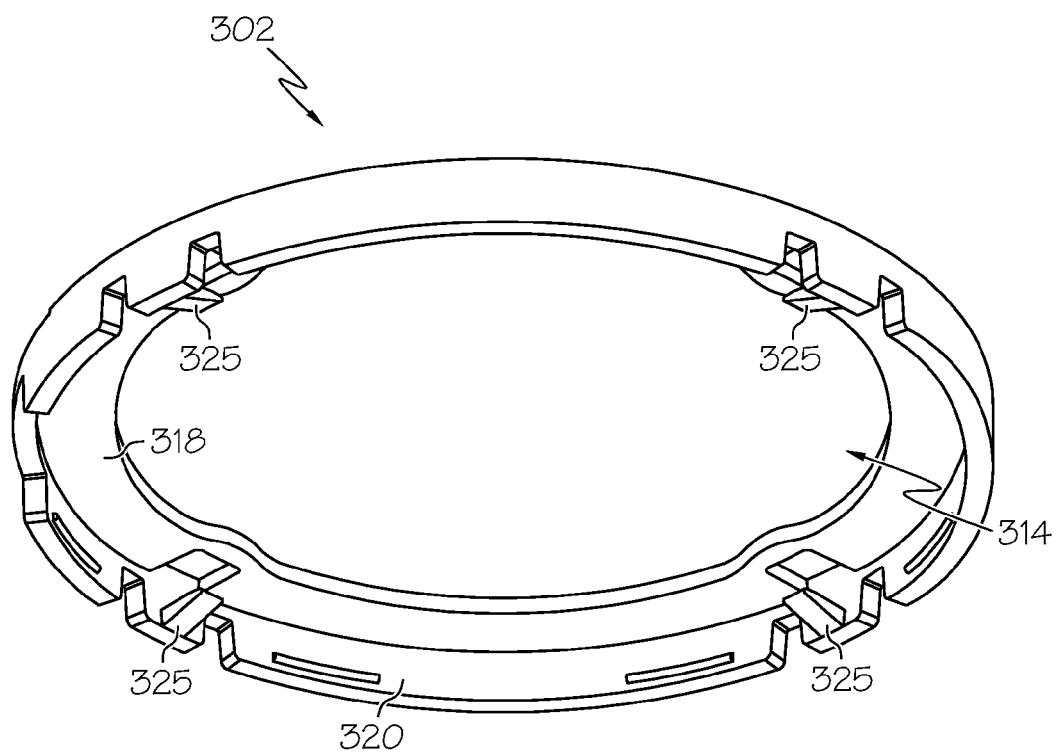
FIG. 13 is a bottom perspective view of the offset element.
Figure 14:
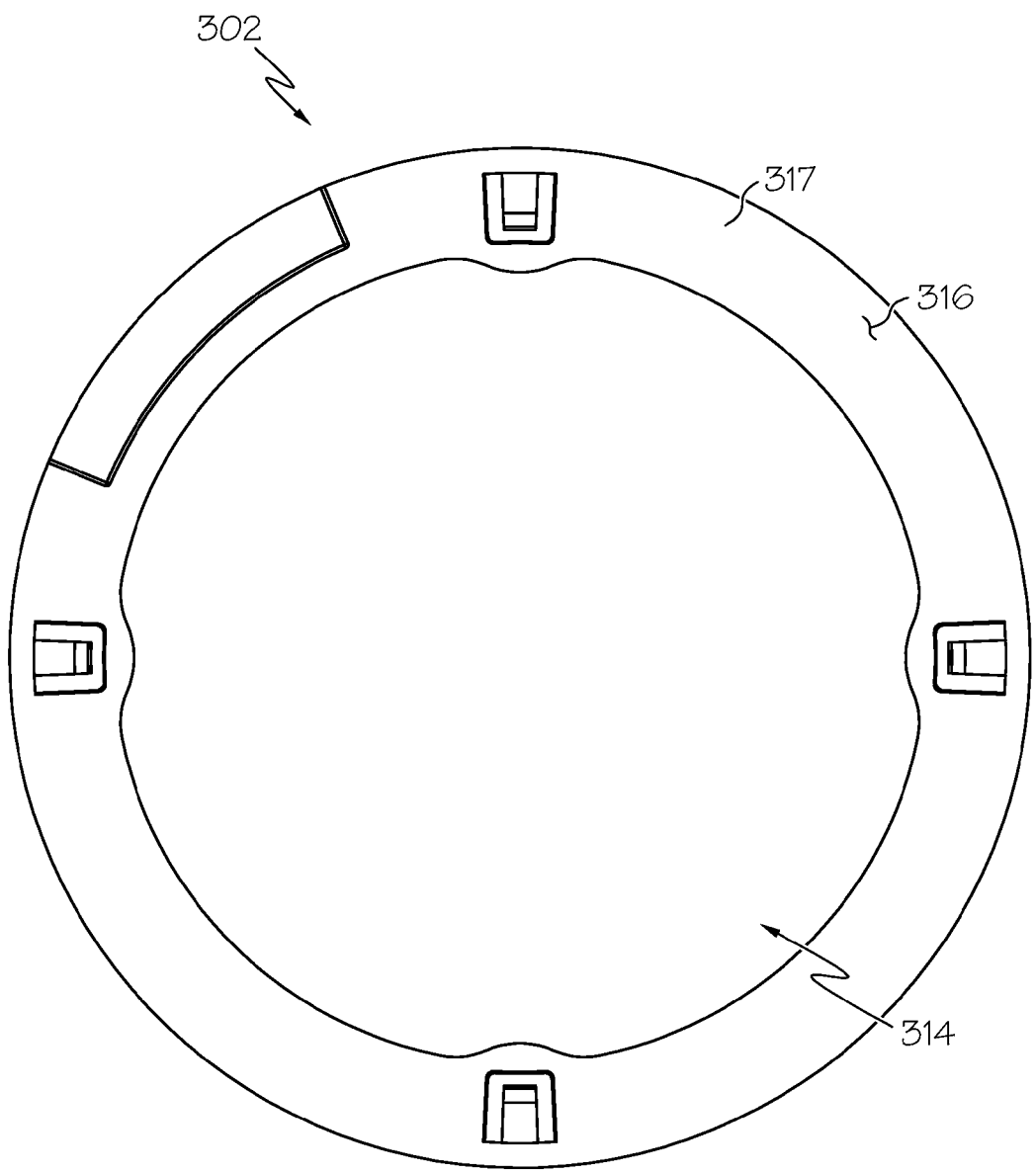
FIG. 14 is a top view of the offset element.
Figure 15:
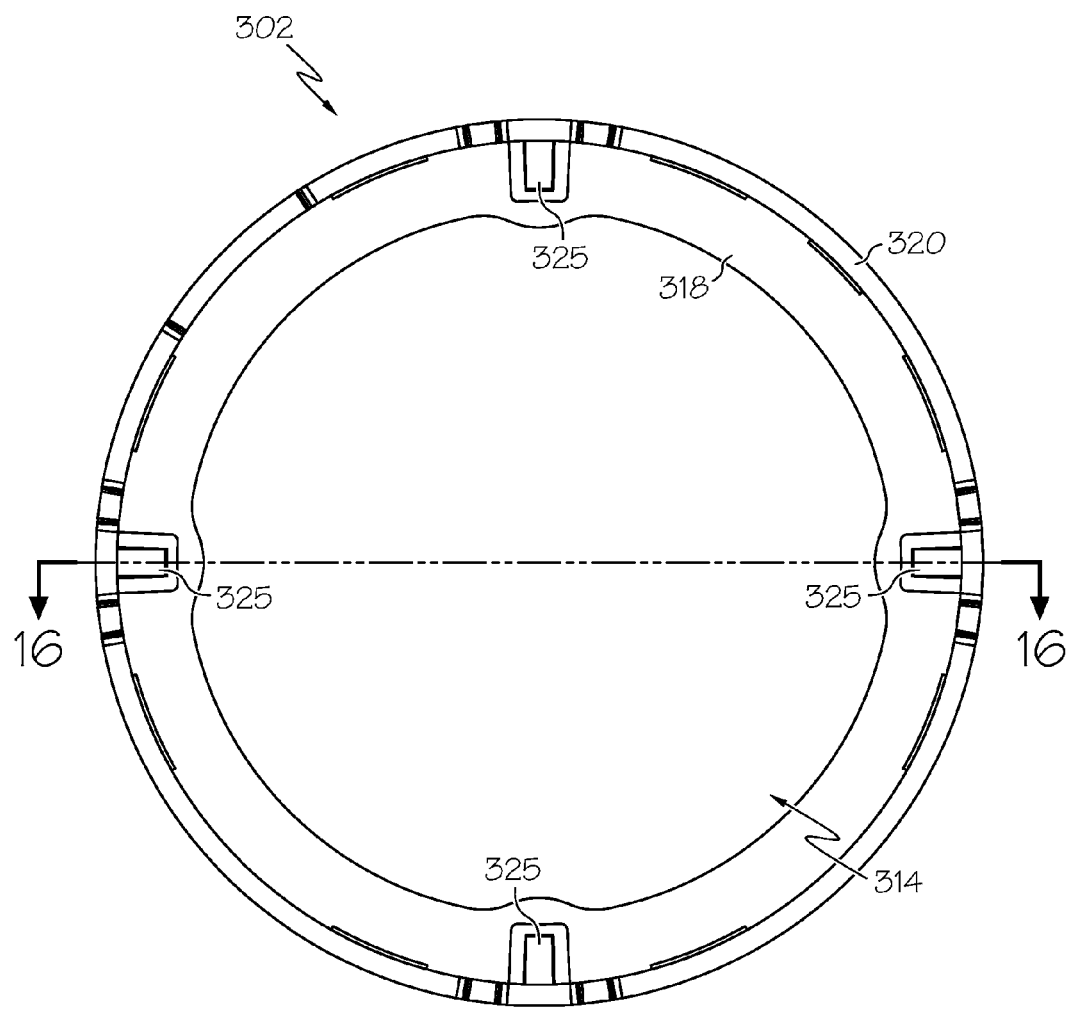
FIG. 15 is a bottom view of the offset element.
Figure 16:
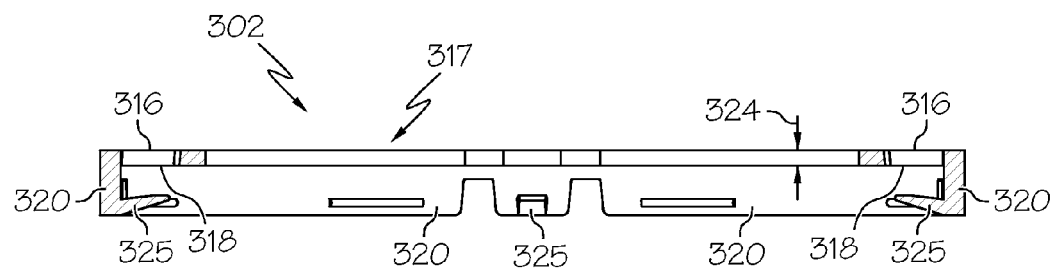
FIG. 16 is a cross sectional view of the offset element, as viewed along line 16-16 of FIG. 15.

When assembled, the carrier substrate 134, the piezoelectric speaker 136, and the offset element 302 together form a subassembly (which may be part of the electronics assembly 122) that can be inserted into the rigid housing 112. Moreover, when assembled, the mounting component 304 compresses the transducer assembly 300 against the interior wall or surface of the housing 112, which causes the piezoelectric speaker 136 to sit firmly against the offset element 302. The offset element 302 is used to maintain the actuator of the piezoelectric speaker 136 in a displaced position relative to the interior surface of the housing 112 (see FIG. 17). FIG. 12 is a top perspective view of the offset element 302, FIG. 13 is a bottom perspective view of the offset element 302, FIG. 14 is a top view of the offset element 302, FIG. 15 is a bottom view of the offset element 302, FIG. 16 is a cross sectional view of the offset element 302 as viewed along line 16-16 of FIG. 15, and FIG. 17 is a cross sectional side view of a portion of the electronics assembly 122 shown in FIG. 2.

Although not always required, the illustrated embodiment of the offset element 302 is a round, generally ring-shaped shim that is shaped and sized for coupling around the outer perimeter of the piezoelectric speaker 136. The offset element 302 is formed from a rigid material such as hard plastic. In certain embodiments, the offset element 302 is formed from the same plastic material (or a similar plastic material) that is used to form the housing 112. For example, both the offset element 302 and the housing 112 may be composed of the same moldable thermoplastic material. Accordingly, the offset element 302 could be realized as a one-piece component having certain physical features integrally formed therein.

The offset element 302 generally includes, without limitation: a flat abutment surface 316 on its top housing side 317; an actuator side 318 (under the top housing side 317) that mates with the piezoelectric speaker 136; and an outer sidewall 320 extending from the actuator side 318. The flat abutment surface 316 physically contacts and mates with a flat interior surface 322 of the rigid housing 112 when the electronics subassembly 122 is inserted into the housing 112, as shown in FIG. 17. The actuator side 318 physically contacts and mates with a portion of the top major side 306 of the piezoelectric speaker 136. Thus, the actuator side 318 and the top housing side 317 of the offset element 302 are separated by an offset thickness 324 (see FIG. 16). Moreover, the opening 314 extends from the actuator side 318 to the top housing side 317, i.e., the height of the opening 314 corresponds to the offset thickness 324.

Figure 17:
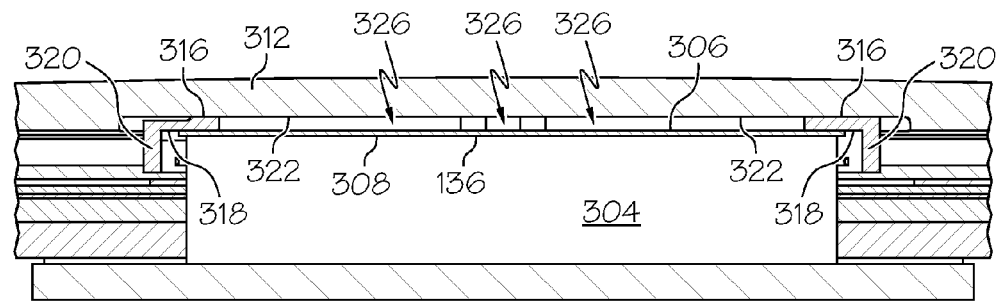
FIG. 17 is a cross sectional side view of a portion of the electronics assembly shown in FIG. 2.

Referring to FIG. 17, when the electronics assembly 122 is installed in the housing 112, the piezoelectric speaker 136 will be enclosed within the housing 112. Moreover, the rim of the offset element 302 will be located between the interior surface 322 of the housing 112 and the piezoelectric speaker 136. For this particular embodiment, the outer sidewall 320 of the offset element 302 surrounds the outer perimeter of the piezoelectric speaker 136. Thus, the piezoelectric speaker 136 is "nested" within the offset element 302 and it resides within an area defined by the outer sidewall 320. The piezoelectric speaker 136 may be held in position using tabs 325, flanges, or other features of the offset element 302 (see FIG. 13, FIG. 15, and FIG. 16).

In accordance with well known principles, the piezoelectric speaker 136 includes an actuator that is electrically controlled to vibrate and generate sound during operation of the fluid infusion device 100. The offset element 302 is designed to provide a resonant cavity 326 for the piezoelectric speaker 136 (see FIG. 17). Notably, the offset element 302, the opening 314, the offset thickness 324, the top major side of the piezoelectric speaker 136, and the interior surface 322 of the housing 112 at least partially define this resonant cavity 326. In practice, the offset element 302, its opening 314, and its offset thickness 324 are shaped, sized, and otherwise dimensioned such that the resonant cavity 326 causes air to resonate at a predetermined frequency in response to activation of the piezoelectric speaker 136. In this regard, the resonant cavity 326 may be designed to function as a "Helmholtz" cavity that is tuned to resonate at the desired frequency.

The use of the offset element 302 accommodates the "end loading" installation of the electronics assembly 122 into the housing 112, while still establishing and maintaining the desired resonant cavity 326. As mentioned previously, the resilient mounting component 304 biases the offset element 302 against the interior surface 322 of the housing 112, as depicted in FIG. 17. Thus, the dimensions of the resonant cavity 326 are maintained after the fluid infusion device 100 has been assembled.

Resilient Cover For Electronics Assembly

Figure 18:
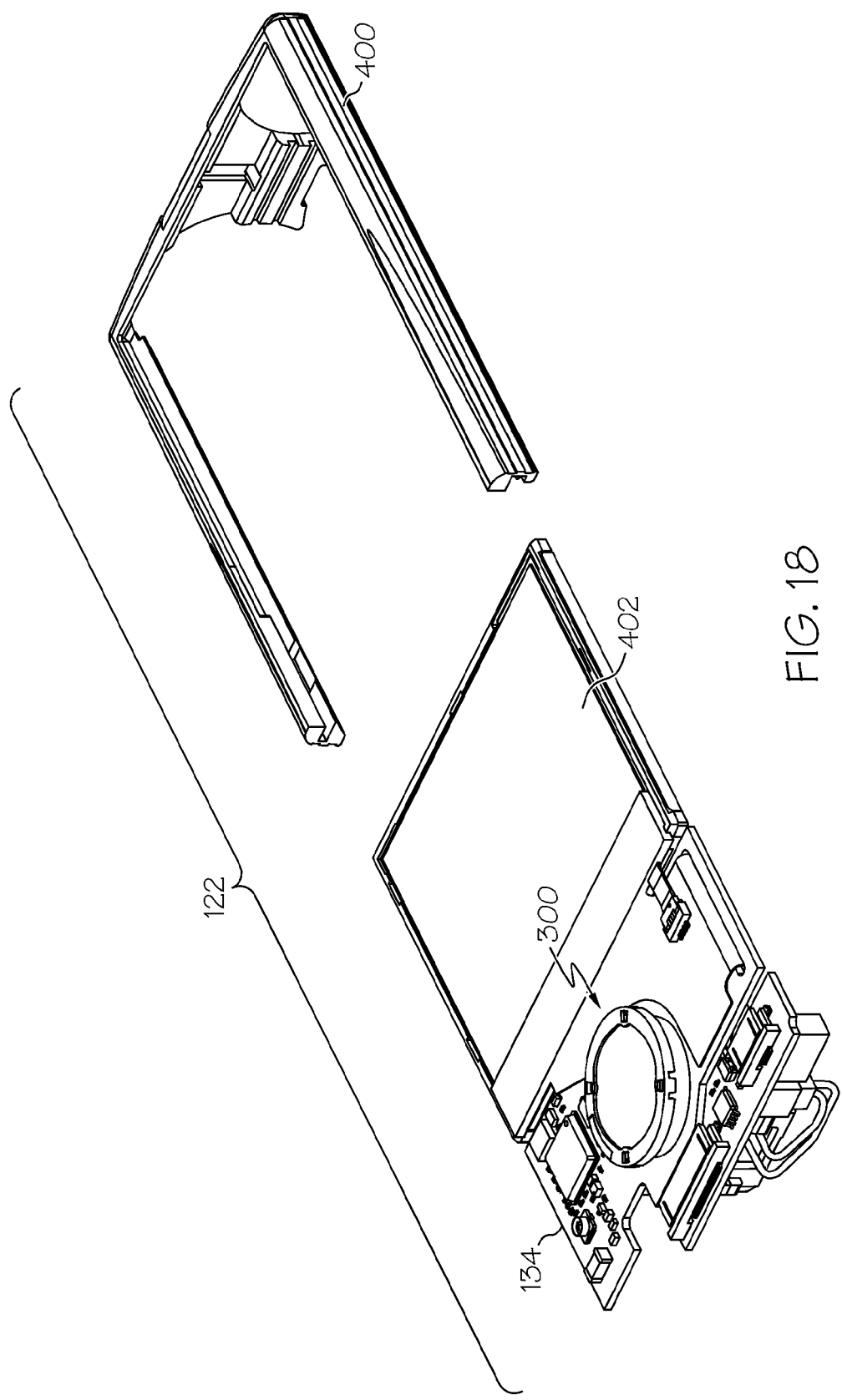
FIG. 18 is an exploded perspective view of the electronics assembly shown in FIG. 2.

Referring again to FIG. 2, the electronics assembly 122 is inserted as a unit into the housing 112. The electronics assembly 122 includes the carrier substrate 134, the transducer assembly 300 mounted to the carrier substrate 134, and other components. In certain embodiments, the electronics assembly 122 includes a resilient cover 400, which is depicted in FIG. 18. Another embodiment of this resilient cover 400 (which lacks the central cross member) is depicted in FIG. 2 and FIG. 11. The resilient cover 400 serves to protect the electronics assembly 122, the display, and other delicate components under "drop and shock" conditions. The resilient cover 400 also serves to center the display within the display window formed in the housing 112. The resilient cover 400 is also suitably designed such that the electronics assembly 122 can be easily installed into the housing 112 with little to no friction. In this regard, the resilient cover 400 may be coated with a lubricant or a friction-reducing substance that facilitates ease of assembly. Moreover, the resilient cover 400 functions as a seal or dust protector for three of the four edges surrounding the display.

The resilient cover 400 is installed onto the electronics assembly 122 such that it frames the liquid crystal display (LCD) assembly 402 and wraps around the various board components. Once installed, the resilient cover 400 absorbs assembly tolerances so that the positions of the LCD assembly 402 and electronics assembly 122 remain substantially fixed during normal handling. The resilient cover 400 also forms a seal between the frame of the LCD assembly 402 and the interior surface of the housing 112, thus preventing dust from settling onto the front glass surface of the LCD assembly 402. During a drop, impact, or shock, the resilient cover 400 absorbs and dissipates kinetic energy, thus protecting the LCD assembly 402 and electronics assembly 122 from damage. The resilient cover 400 is also suitably designed to "spring" back into position such that the LCD display returns to its nominal centered position relative to the display window of the housing 112.

Assembly Shim

The fluid infusion device 100 is assembled by loading its internal components into the base end 116 of the housing 112 (see FIG. 2). In this regard, the fluid infusion device 100 is an end-loaded device. Thus, the various internal components are inserted into the housing 112 and capped by another component, e.g., the housing end cap 114.

The main internal component, the electronics assembly 122, should be readily installable with minimal force, be held in place so that the LCD display aligns with the display window of the housing 112, and be retained in place firmly during operation. Accordingly, it is desirable to have an electronics assembly 122 that is easily inserted and, when inside the housing 112, held firmly so that drops, shocks, vibrations, etc. do not significantly shift the position of the LCD display. Thus, the elastomeric resilient cover 400 and case bottom dampener (described below) at the final assembly stage should be compressed within the housing 112. The end load design of the fluid infusion device 100 results in compression of the resilient cover 400 as it enters the housing 112. The elastomeric material of the resilient cover 400 has a relatively high coefficient of friction, requiring high assembly forces during manufacturing, if not coated with friction-reducing coatings.

Figure 19:
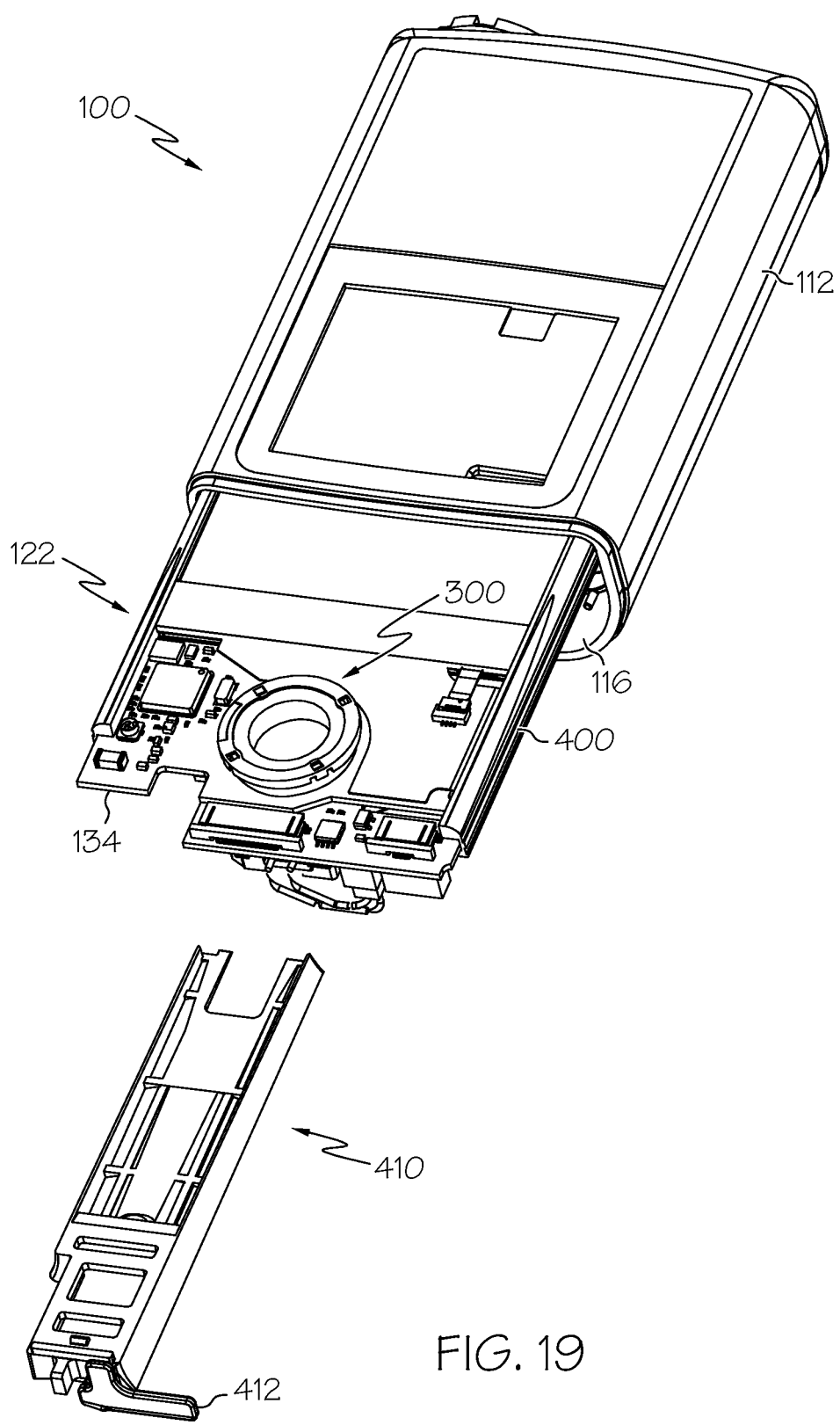
FIG. 19 is an exploded perspective view of the fluid infusion device.
Figure 20:
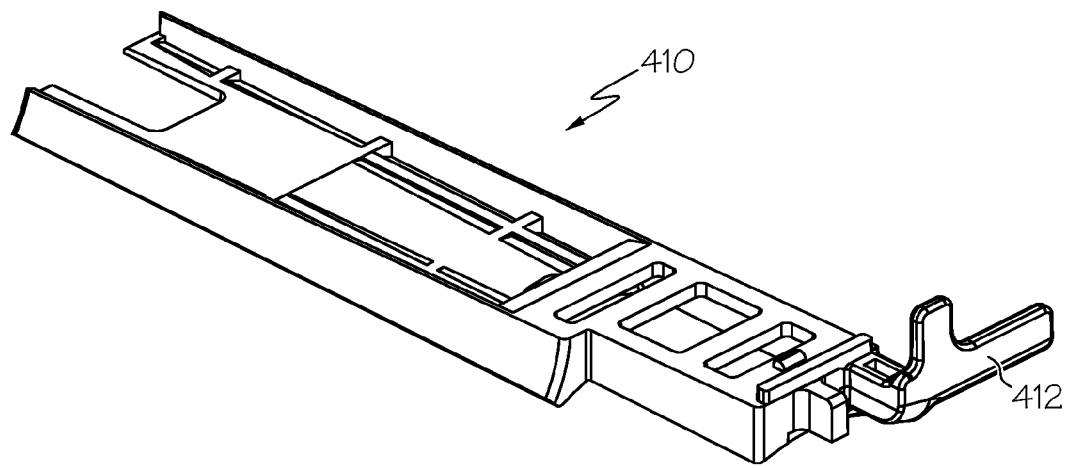
FIG. 20 is a perspective view of an assembly shim suitable for use with the fluid infusion device.

The fluid infusion device 100 also employs an assembly shim 410 that addresses some of the manufacturing issues mentioned above. FIG. 19 is an exploded perspective assembly view of the fluid infusion device 100 during a step in the manufacturing process, and FIG. 20 is a perspective view of the assembly shim 410 by itself. When the assembly shim 410 is used, the electronics assembly 122 can be end-loaded into the housing 112 with little to no force or pressure. In other words, the electronics assembly 122 by itself does not engage the housing with an interference fit. Instead, when the electronics assembly 122 is fully inserted into the housing 112, it remains relatively loose and "floating" in the housing 112. Thereafter, the assembly shim 410 is inserted into the housing 112 below the electronics assembly 122, as depicted in FIG. 19. The assembly shim 410 is formed of thermoplastic material with a lower coefficient of friction than that of the resilient cover 400. The assembly shim 410 biases the electronics assembly 122 upward (i.e., toward the display window of the housing 112), and "locks" the electronics assembly 122 in place within the housing 112. Once positioned in this manner, the electronics assembly 122 does not move within the housing 112. The biasing of the electronics assembly 122 in this manner also sets the resilient cover 400 against the interior surfaces of the housing 112, which provides a degree of dust protection.

The assembly shim 410 also serves as a contact point for the case bottom dampener, which is described below in a separate section of this specification. Accordingly, the amount of compressive force imparted to the assembly shim 410 (at the bottom of the housing 112) can be chosen by design of the assembly shim 410 and the case bottom dampener.

The assembly shim 410 also facilitates easy repairs and rework of the fluid infusion device 100. When the assembly shim 410 is removed from the housing 112, the electronics assembly 122 can be easily removed from the housing 112 for inspection, repair, or replacement without using tweezers or pliers, and without having to bump or impact the housing 112 to dislodge the electronics assembly 122.

The assembly shim 410 also functions as a cable or wire management device for the fluid infusion device 100. In this regard, when the electronics assembly 122 is inserted into the housing 112, there are various flex cables and wires protruding from the base end 116 of the housing 112. These electrical conductors can be cumbersome to work around and make it difficult to affix the housing end cap 114 to the housing 112 (the cables and wires might interfere with the bonding or welding of the of the housing end cap 114 to the housing 112, e.g., contacting the housing end cap 114 before a weld is fully initiated). Referring to FIG. 20, the assembly shim 410 has an arm 412 that is configured to hold the various ribbon cables, wires, and other electrical conductors in their designated positions during and after assembly. The shape, size, and form factor of the arm 412 contemplates the relative positioning and intended routing of the cables, wires, and conductors when the electronics assembly 122 and the assembly shim 410 are fully inserted into the housing 112. In this manner, the assembly shim 410 eliminates the need for assembly technicians to hold or manipulate loose cables and wires between assembly steps and/or between assembly stations, and the assembly shim 410 allows the housing end cap 114 to be easily attached to the housing 112.

Motor Support Cap

Figure 21:
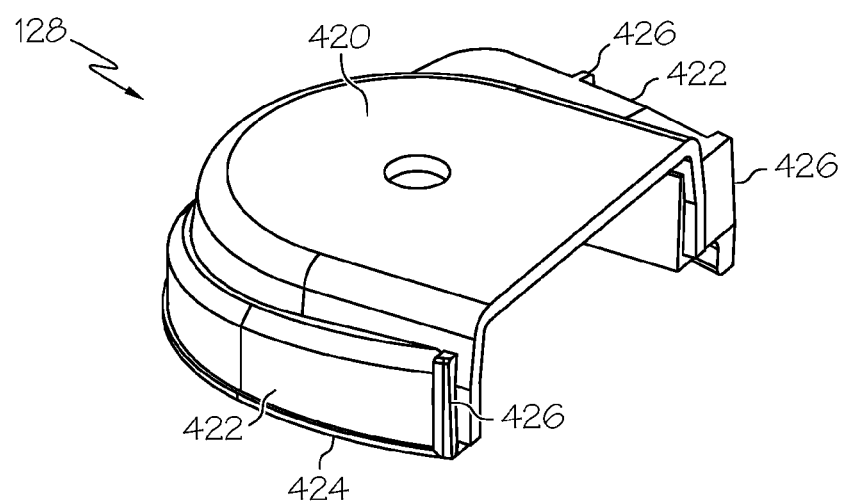
FIG. 21 is a perspective view of a motor support cap suitable for use with the fluid infusion device.
Figure 22:
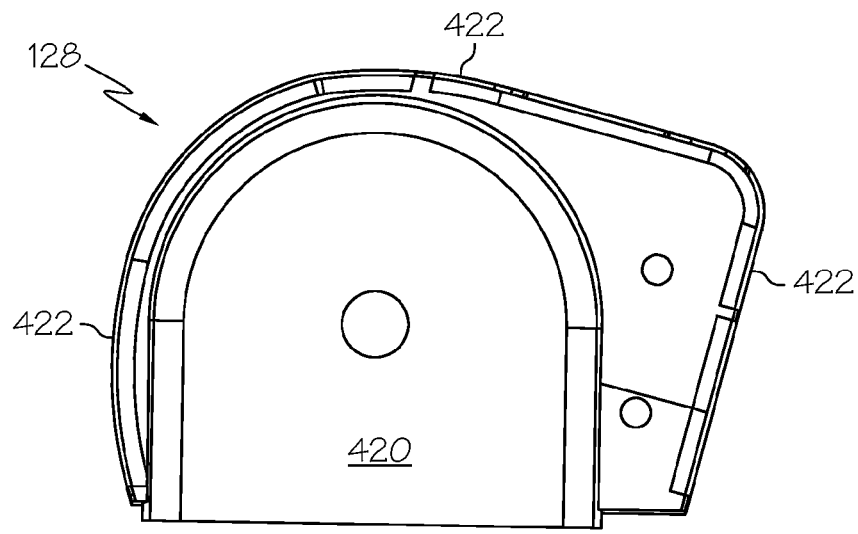
FIG. 22 is a top view of the motor support cap.
Figure 23:
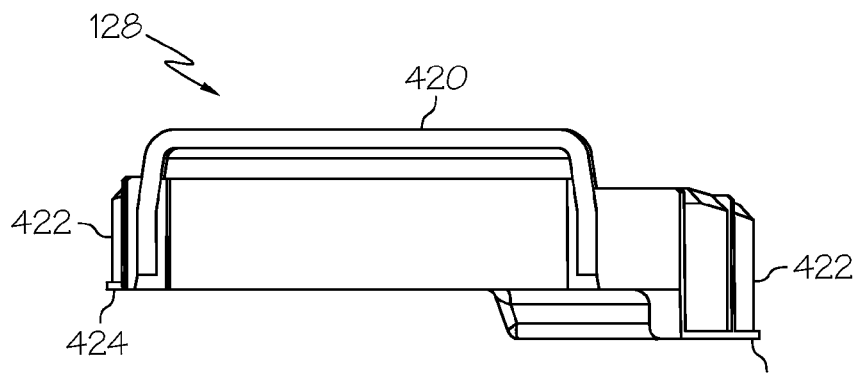
FIG. 23 is a front elevation view of the motor support cap.
Figure 24:
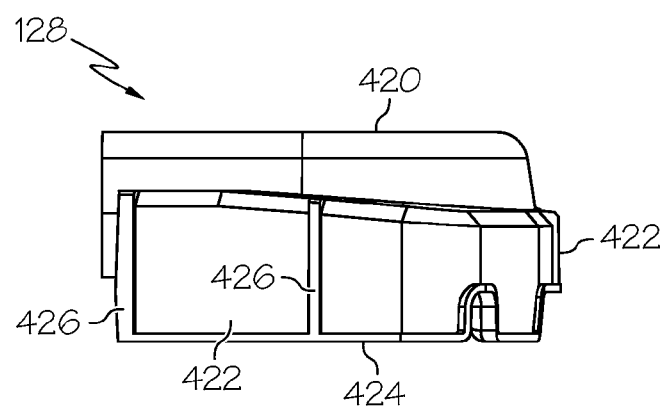
FIG. 24 is a side elevation view of the motor support cap.
Figure 25:
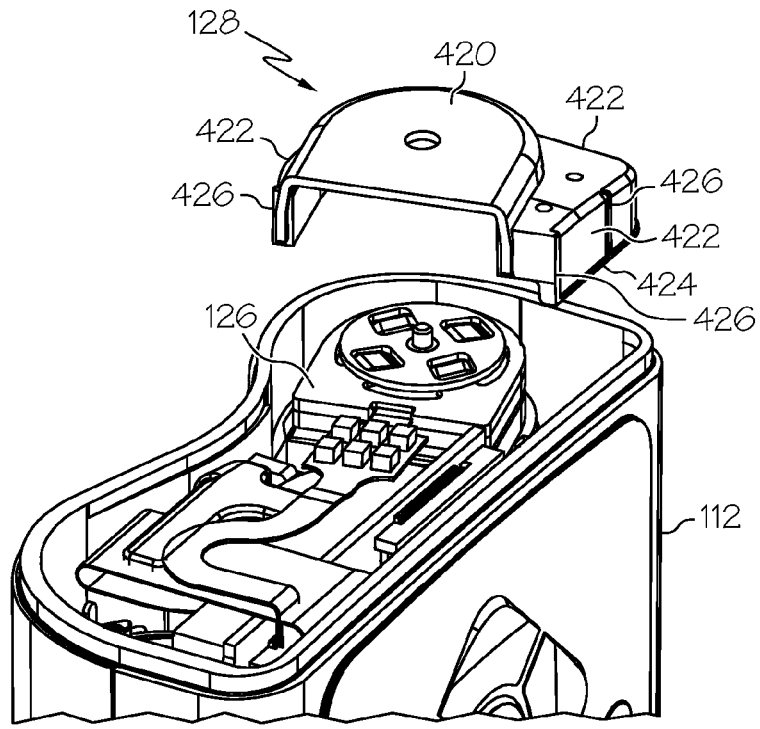
FIG. 25 is an exploded perspective view of a portion of the fluid infusion device.
Figure 26:
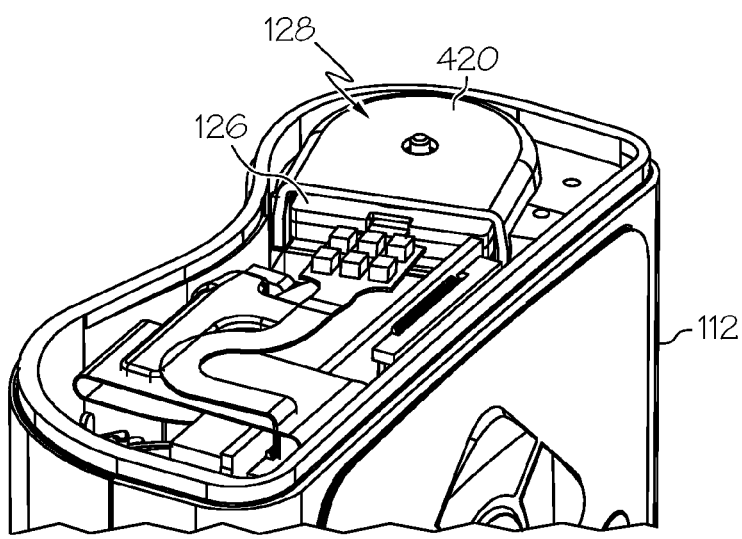
FIG. 26 is a perspective view of the fluid infusion device shown in FIG. 25, after installation of the motor support cap.

As mentioned above with reference to FIG. 2, the fluid infusion device 100 may employ a motor support cap 128 that supports the drive motor assembly 124 and covers a portion of the force sensor 126. FIG. 21 is a perspective view of the motor support cap 128 by itself, FIG. 22 is a top view of the motor support cap 128, FIG. 23 is a front elevation view of the motor support cap 128, and FIG. 24 is a side elevation view of the motor support cap 128. FIG. 25 is an exploded view of the fluid infusion device 100, showing the motor support cap 128 in an uninstalled state, and FIG. 26 is a perspective view of the fluid infusion device 100 showing the installed state of the motor support cap 128.

The motor support cap 128 removes slack from assembly tolerances associated with the drive system, namely, the drive motor assembly 124. The motor support cap 128 is designed to tolerate very high impact load in drop and shock conditions. The motor support cap 128 is an insert molded component that has a high strength steel stamping 420 formed into the desired shape. A polycarbonate material is molded over the stamping 420 in a form that fits inside the housing 112 in the region below the drive motor assembly 124. Polycarbonate is used because of its optical properties so that ultraviolet (UV) light can shine through and cure an adhesive to secure the motor support cap 128 to the inside wall of the housing 112. The composite combination of metal and plastic provides the required rigidity and assembly flexibility.

For assembly, the motor support cap 128 is placed such that it covers and supports the end of the drive motor assembly 124 and the force sensor 126 (see FIG. 25). Once the motor support cap 128 is in place, a UV cure adhesive is applied around the polycarbonate perimeter 422 of the motor support cap 128. In its uncured state, the UV adhesive can run down the side in a gap between the motor support cap 128 and the inner wall of the housing 112 (assuming that the housing 112 is held in an upright orientation such as that depicted in FIG. 25). To keep the adhesive from running too far into the housing 112, and possibly staying on the drive motor assembly 124, a horizontal rib 424 is molded around the bottom of the perimeter 422 to act as a dam for the adhesive. Moreover, vertical ribs 426 are formed in the polycarbonate (at the ends and intermittently around the perimeter 422) to compartmentalize the UV adhesive and to minimize build up of the adhesive. The vertical ribs 426 help to create and maintain the desired gap for the adhesive. This allows delivery of the UV cure adhesive to be more evenly distributed and to completely fill in the gap formed between the motor support cap 128 and the housing 112. The motor support cap 128 has the added benefit of eliminating a leak path from the housing 112. Moreover, the shock load from the drive system is transferred to the housing 112 and not the housing end cap 114. This allows the dispersion of the load to the larger mass of the housing 112 instead of the smaller housing end cap 114.

Case Bottom Dampener

Figure 27:
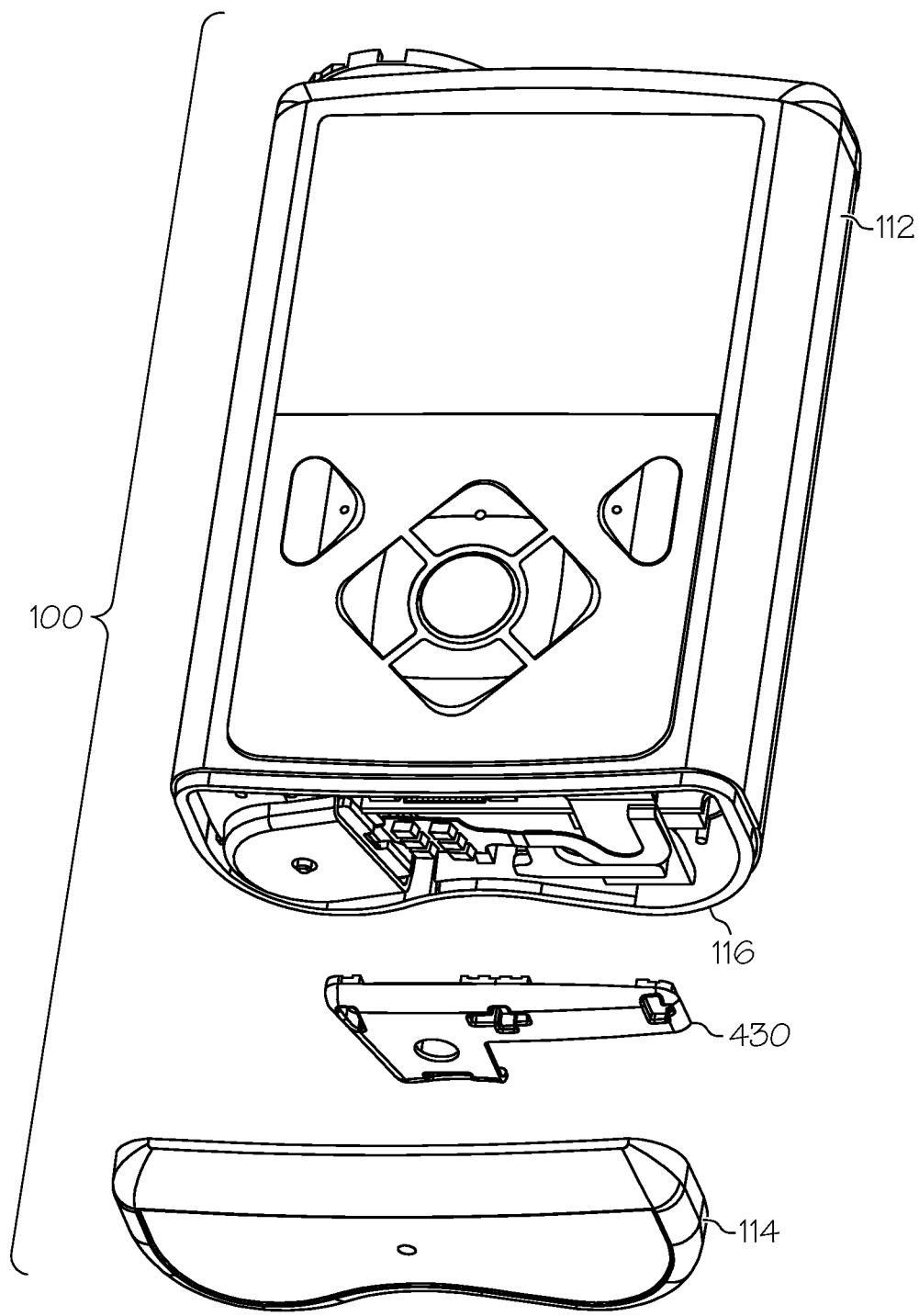
FIG. 27 is an exploded front perspective view of the fluid infusion device, showing a case bottom dampener.
Figure 28:
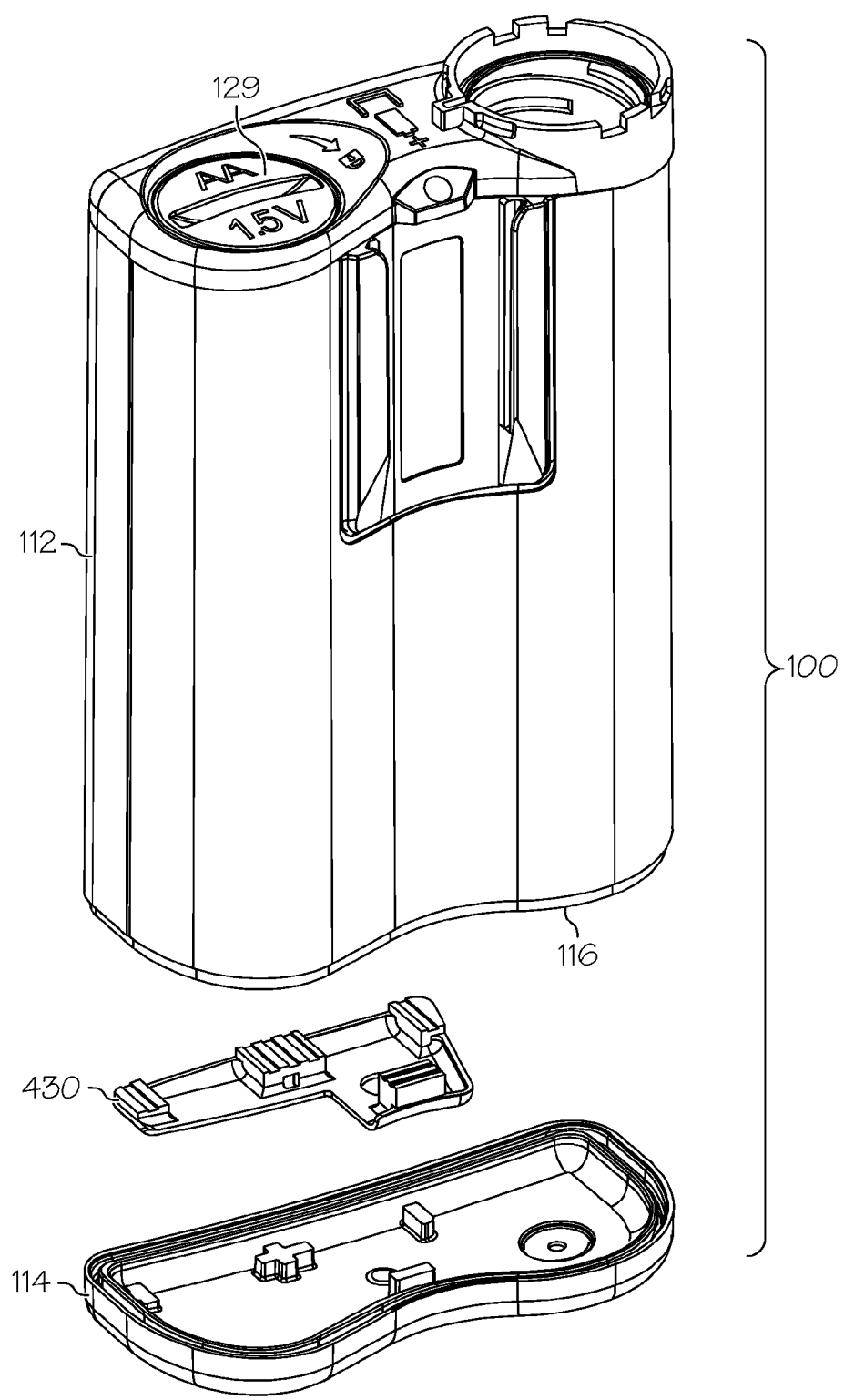
FIG. 28 is an exploded rear perspective view of the fluid infusion device, showing the case bottom dampener.

Certain embodiments of the fluid infusion device 100 employ a cushioning element between the housing end cap 114 and the internal components inside the housing 112. In this regard, FIG. 27 is an exploded front perspective view of the fluid infusion device 100, and FIG. 28 is an exploded rear perspective view of the fluid infusion device 100. FIG. 27 and FIG. 28 both depict the fluid infusion device 100 before the housing end cap 114 has been attached to the base end 116 of the housing 112. These figures also show a case bottom dampener 430 prior to installation. The case bottom dampener 430 is formed from a resilient material such as rubber, polyurethane, foam, or the like. The case bottom dampener 430 has features and characteristics (e.g., ribs, protrusions, shoulders) that facilitate positioning relative to corresponding features formed on the housing end cap 114 and/or corresponding features of the internal components of the fluid infusion device 100.

When assembled, the electronics assembly 122 (see FIG. 2) is located inside the housing 112 and is positioned by one or more resilient components (dampeners) such as the assembly shim 410 described above. The case bottom dampener 430 is installed onto the interior surface of the housing end cap 114 before the housing end cap 114 is attached to the housing 112. The case bottom dampener 430 provides a slight positional bias and loading upon the electronics assembly 122 within the housing 112. This loading helps to absorb assembly tolerances so that the position of the electronics assembly 122 is fixed during normal handling of the fluid infusion device 100. During a drop, impact or shock, the case bottom dampener 430 acts to absorb and dissipate kinetic energy, thus protecting the electronics assembly 122 from damage. The case bottom dampener also provides enough rebound force to push the electronics assembly 122 back into its nominal position, thus ensuring that the LCD display is centered with respect to the display window of the housing 112.

Thermoplastic Adhesive For Housing End Cap

Figure 29:
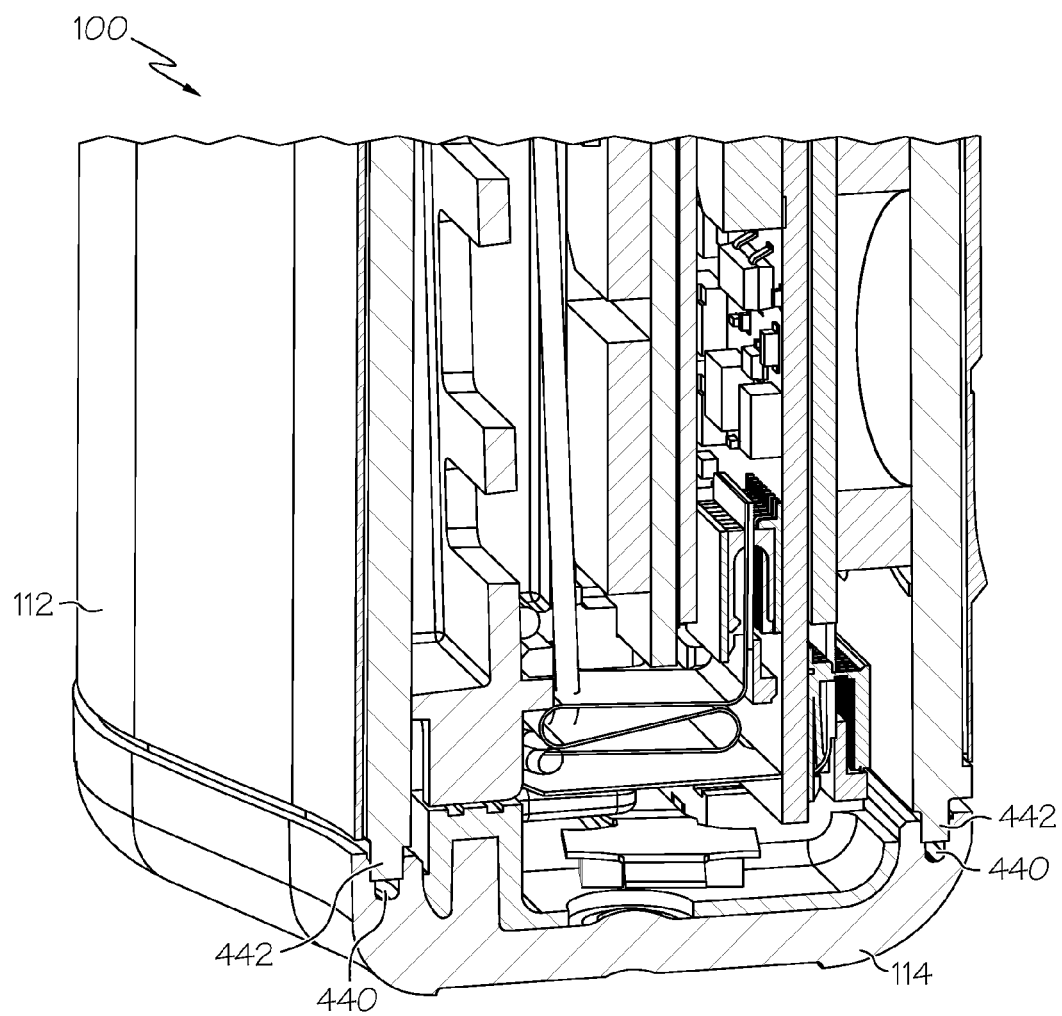
FIG. 29 is a perspective cross sectional view of the bottom end of the fluid infusion device.

As mentioned previously, the fluid infusion device 100 is assembled by end-loading all internal components into the housing 112 and bonding the housing end cap 114 onto the housing 112 in order to seal the unit. In preferred embodiments, the housing end cap 114 is ultrasonically welded to the end of the housing 112 utilizing a double shear weld joint to produce a water resistant seal (to satisfy specifications such as, for example, IPX8). This bond interface can be further improved by adding a bead of thermoplastic adhesive to the groove within the housing end cap 114, as depicted in FIG. 29. As shown in FIG. 29, the housing end cap 114 includes a groove 440 around its edge; this groove 440 mates with a corresponding lip 442 of the housing 112.

During assembly, the thermoplastic adhesive is applied to the groove 440 and/or to the lip 442 before the housing end cap 114 is secured to the housing 112. Thereafter, the joint is subjected to an ultrasonic welding process. The heat generated during the ultrasonic welding operation serves to melt the thermoplastic adhesive, causing it to flow into any remaining crevasses between the housing 112 and the housing end cap 114. The flow and subsequent solidification of the thermoplastic adhesive improves the sealing capability as well as the strength of the bond between the housing 112 and the housing end cap 114.

Keypad Overlay Sealing And Graphic Keypad Overlay

Figure 30:
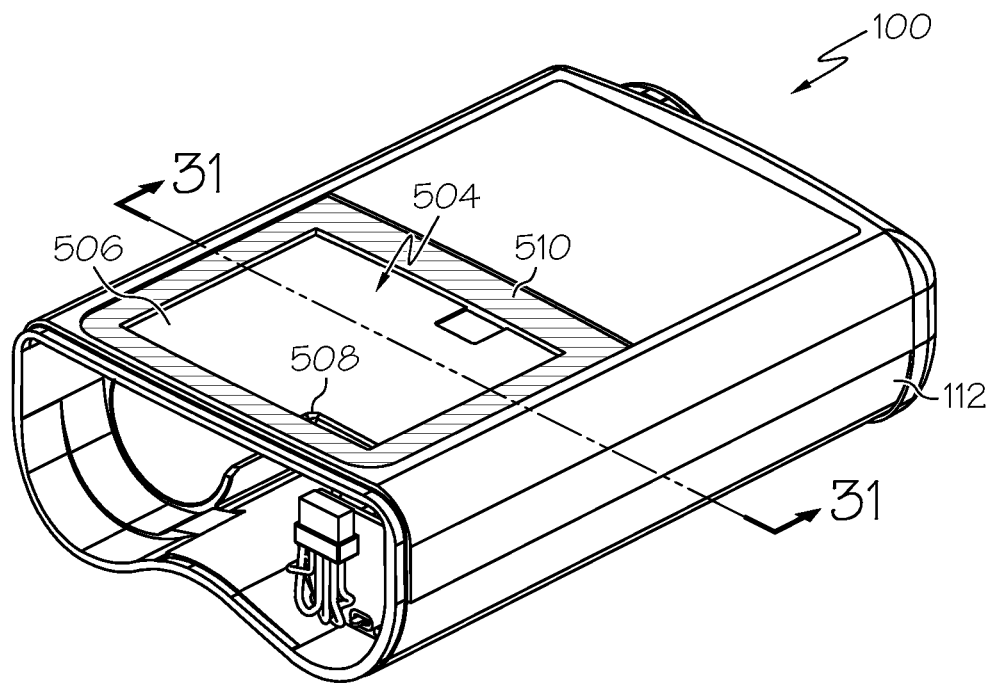
FIG. 30 is a perspective front view of the housing of the fluid infusion device.
Figure 32:
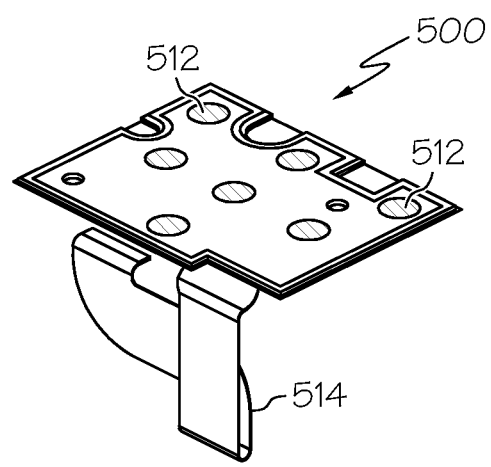
FIG. 32 is a perspective front view of a membrane keypad assembly suitable for use with the fluid infusion device.
Figure 31:
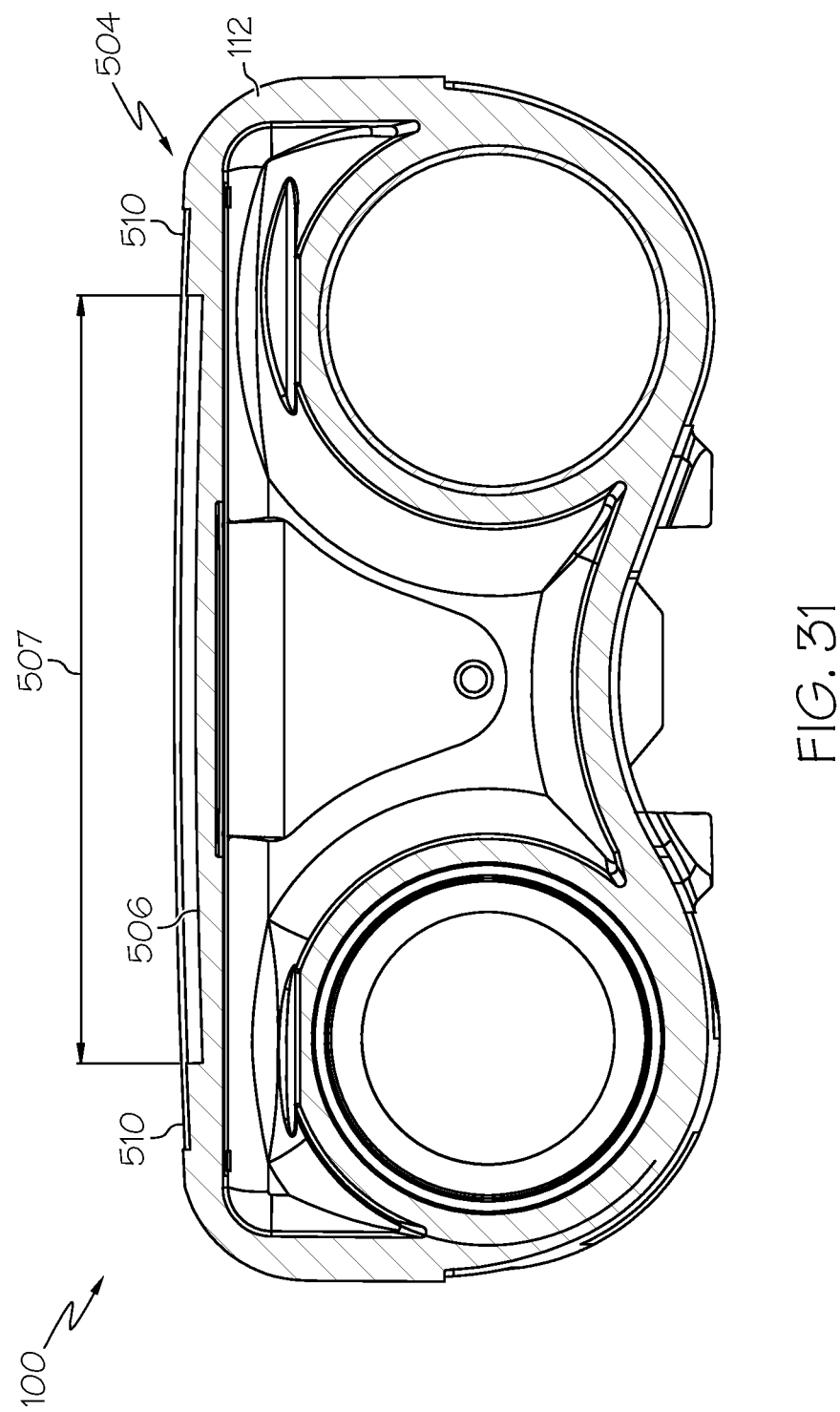
FIG. 31 is a cross sectional view of the housing, as viewed from line 31-31 in FIG. 30.
Figure 33:
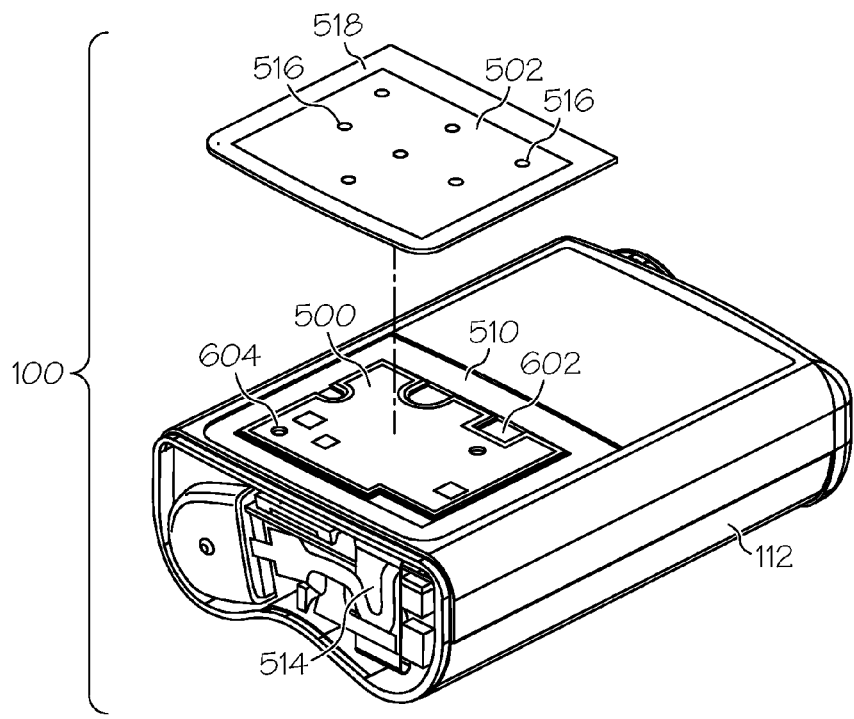
FIG. 33 is a perspective front view of the fluid infusion device prior to installation of a keypad actuator layer.
Figure 34:
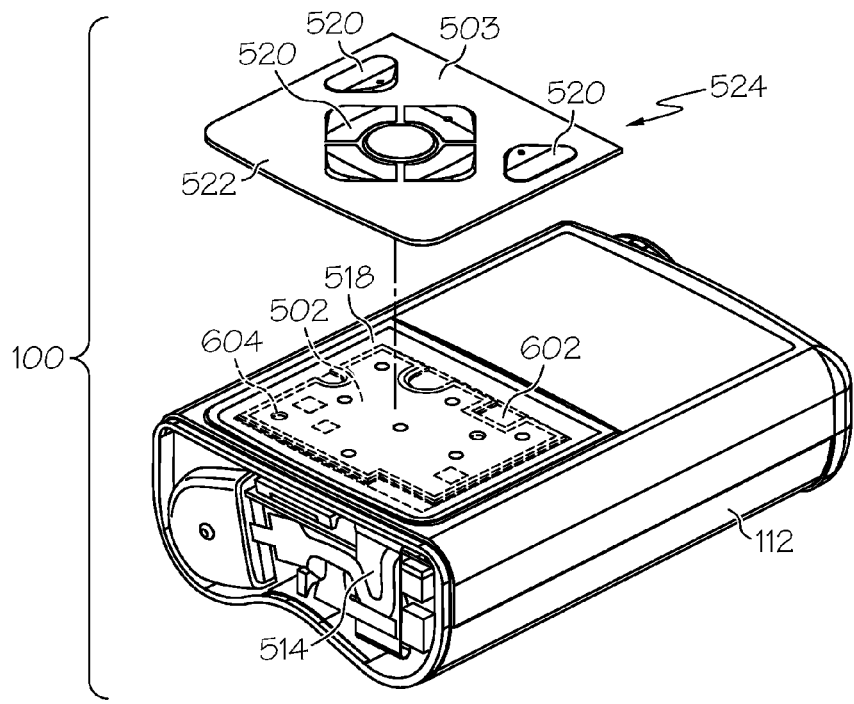
FIG. 34 is a perspective front view of the fluid infusion device prior to installation of a graphic keypad overlay.

In contrast to conventional designs that use a graphical keypad overlay to form a water resistant seal with the device housing, the fluid infusion device 100 uses a distinct sealing element and/or a keypad actuator layer to form the seal. FIGS. 30-33 illustrate an exemplary embodiment that includes this feature. FIG. 30 is a perspective front view of the housing 112 of the fluid infusion device 100, FIG. 31 is a cross sectional view of the housing 112 as viewed from line 31-31 in FIG. 30, FIG. 32 is a perspective front view of a membrane keypad assembly 500 suitable for use with the fluid infusion device 100, FIG. 33 is a perspective front view of the fluid infusion device 100 prior to installation of a keypad actuator layer 502, and FIG. 34 is a perspective front view of the fluid infusion device 100 prior to installation of a graphic keypad overlay 503.

Referring to FIG. 30 and FIG. 31, the housing 112 has a front face 504, which generally corresponds to the front major side of the fluid infusion device 100, i.e., the side having the display and primary user interface features. In certain embodiments, the front face 504 includes one or more mounting features or elements formed therein. For example, the illustrated embodiment includes a keypad mounting cavity 506 integrally formed in the front face 504 of the housing 112. The keypad mounting cavity 506 is one suitable implementation of a keypad mounting area that is shaped and sized to accommodate the keypad assembly 500. The keypad mounting cavity 506 is preferably dimensioned such that the keypad assembly 500 fits within its border. In this regard, the illustrated example employs a rectangular keypad mounting cavity 506 having a depth that allows the keypad assembly 500 to sit inside the keypad mounting cavity 506 without protruding. In FIG. 31, the keypad mounting cavity 506 is centrally located and has a width that is identified by the arrow 507. The housing 112 may also have a hole or a slot 508 formed therein to accommodate a flex circuit tail, wires, or other electrical conductors of the keypad assembly 500. As shown in FIG. 30, the slot 508 is located within the area defined by the keypad mounting cavity 506.

The front face 504 also includes a sealing surface surrounding the keypad mounting cavity 506. For this particular embodiment, the sealing surface is realized as a sealing rim 510 that is integrally formed as part of the housing 112 (the sealing rim 510 corresponds to the shaded area in FIG. 30). The sealing rim 510 is located outside and around the keypad mounting cavity 506, and the upper surface of the sealing rim 510 resides above the base of the keypad mounting cavity 506, as shown in FIG. 31. The sealing rim 510 is shaped, sized, and dimensioned to accommodate a sealing element and/or the keypad actuator layer 502 of the fluid infusion device 100. In this regard, the sealing rim 510 is preferably dimensioned such that the sealing layer fits within its border. The illustrated example employs a rectangular ring-shaped sealing rim 510 having a depth that allows the sealing member to sit recessed within the housing 112. FIG. 31 depicts how the sealing rim 510 extends beyond the keypad mounting cavity 506 (the sealing rim 510 defines a relatively shallow step outside the perimeter of the keypad mounting cavity 506.

Referring now to FIG. 32, the keypad assembly 500 is preferably realized as a membrane keypad assembly, which can be fabricated in accordance with well known techniques and technology. The keypad assembly 500 includes actuation components 512 integrated therein, and a flex circuit tail 514 having electrical conductors coupled to the actuation components 512. In a practical embodiment, the actuation components 512 may be realized as metal domes arranged in two dome arrays, stacked to create a double-stacked metal dome assembly. In certain implementations, the flex circuit tail 514 is formed from a polyimide material that serves as a carrier for electrical conductors. Although the exact number of actuation components 512 may vary from one device to another, the illustrated embodiment of the keypad assembly 500 has seven. After assembly of the fluid infusion device 100 is complete, the actuation components 512 can be manipulated and actuated to control operation of the fluid infusion device 100.

During assembly of the fluid infusion device 100, the membrane keypad assembly 500 is positioned in the keypad mounting cavity 506 of the housing 112, and it is electrically connected such that it interfaces with the interior electronics assembly 122 by way of the polyimide flex circuit tail 514. In this regard, the flex circuit tail 514 is routed through the slot 508 before the keypad assembly 500 is secured to the housing 112 (see FIG. 33). An adhesive or double backed tape can be used to affix the keypad assembly 500 to the housing 112.

Referring to FIG. 33, the keypad actuator layer 502 serves as a sealing element for the keypad assembly 500, and it inhibits fluid incursion into the housing 112. The keypad actuator layer 502 is formed from a flexible material such as plastic, polyester, polyurethane, or the like. In certain preferred embodiments, the keypad actuator layer 502 is non-decorative, non-cosmetic, and free of printed graphics (e.g., ink-based graphics). In particular, the bottom surface of the keypad actuator layer 502 should be free of decoration, ink, paint, or other substances that are prone to peeling or flaking, for reasons explained below.

The keypad actuator layer 502 includes protrusions 516 corresponding to the actuation components 512 of the underlying keypad assembly 500. These protrusions 516 may extend from the upper surface and/or the lower surface of the keypad actuator layer 502. After the keypad actuator layer 502 is installed overlying the keypad assembly 500, the protrusions 516 will be overlying and aligned with their respective actuation components 512. The protrusions 516 facilitate actuation of the underlying actuation components 512 by concentrating user-applied forces at or near the actuation components 512.

The keypad actuator layer 502 has a perimeter area 518 that extends beyond the keypad assembly 500. For the illustrated embodiment, the perimeter area 518 corresponds to an outer rectangular ring-shaped boundary of the keypad actuator layer 502. Accordingly, the keypad actuator layer 502 completely covers and overlies the keypad assembly 500 (after assembly), as shown in FIG. 34. In this regard, the keypad actuator layer 502 is shaped and sized to fit within the shallow depression formed by the sealing rim 510. Moreover, the perimeter area 518 of the keypad actuator layer 502 is coupled to the sealing rim 510 in a manner that forms a fluid resistant seal between the housing 112 and the keypad actuator layer 502.

During assembly of the fluid infusion device 100, a suitable adhesive (e.g., a polyester thermoplastic adhesive) is applied to the bottom surface of the perimeter area 518 and/or to the sealing rim 510, and the keypad actuator layer 502 is properly aligned and placed overlying the keypad assembly 500, such that the perimeter area 518 is aligned with the sealing rim 510. Thereafter, pressure and heat are applied to the top surface of the perimeter area 518 overlying the sealing rim 510, resulting in the melting, curing, or activation of the thermoplastic adhesive and the bonding of the keypad actuator layer 502 to the sealing rim 510 of the housing 112. The resulting plastic-to-plastic bond forms a fluid resistant seal between the housing 112 and the keypad actuator layer 502, which inhibits fluid such as water from reaching the underlying keypad assembly 500 or internal electronics. Notably, the lack of printed graphics, ink, and other removable substances on at least the perimeter area 518 of the keypad actuator layer 502 enhances the integrity, reliability, and robustness of this seal.

The embodiment described here uses the keypad actuator layer 502 as the sealing layer. Alternatively (or additionally), a distinct sealing element or layer could be used to form the water resistant seal at the housing 112. For example, a sealing film having an appropriate perimeter area could be applied overlying the keypad assembly 500 and the keypad actuator layer 502, where the sealing film (rather than the keypad actuator layer 502) is bonded to the sealing rim 510 of the housing 112. For the same reasons mentioned above, the sealing film should be free of any printed graphics, ink, or other substances that might peel or flake away.

Referring to FIG. 34, the graphic keypad overlay 503 is applied to the top surface of the keypad actuator layer 502 by use of pressure sensitive adhesive, double backed tape, or the like. For this particular embodiment, the graphic keypad overlay 503 provides no sealing function and is applied to the fluid infusion device 100 near the end of the manufacturing process. Moreover, the graphic keypad overlay 503 is designed to be easily removable and replaceable to accommodate user customization and personalization. This also facilitates the use of different labeling, branding, and color schemes. The relief geometry of the graphic keypad overlay 503 is customizable to allow different aesthetics, tactile feel, and haptic response. Such customization allows generic fluid infusion devices to be created and stocked and thereafter customized with an appropriately stylized graphic keypad overlay 503 to create a specific final assembly appearance.

During assembly, the graphic keypad overlay 503 is adhered to the keypad actuator layer 502 (or to whatever sealing element is used) in the desired orientation. In this regard, the graphic keypad overlay 503 will typically include graphical representations 520 corresponding to the underlying protrusions 516 and the underlying actuation components 512. Thus, the graphical representations 520 are aligned with the actuation components 512 to provide visual guidance to the user. In certain embodiments, the graphic keypad overlay 503 is formed from a clear plastic film having a top surface 522, a bottom surface 524, and graphics printed on or otherwise applied to the bottom surface 524. Accordingly, the graphic keypad overlay 503 is adhered to the keypad actuator layer 502 such that the bottom surface 524 and the graphics face the keypad actuator layer 502, and such that the top surface 522 is exposed. This arrangement protects the graphics, which remain visible through the clear plastic film that forms the graphic keypad overlay 503.

As mentioned above, the graphic keypad overlay 503 is removably adhered to the keypad actuator layer 502 to facilitate replacement or "skinning" of the fluid infusion device 100. In this regard, the fluid infusion device 100 or its case assembly could be provided as a kit with a plurality of different graphic keypad overlays, each having a visually distinct set of graphical features corresponding to the actuation components 512, and each being configured for removable adhesion to the keypad actuator layer 502. In practice, therefore, the adhesive used for the graphic keypad overlay 503 should be weaker than the adhesive used to secure the keypad actuator layer 502 to the sealing rim 510. In other words, it may be desirable to intentionally establish a temporary bond between the graphic keypad overlay 503 and the keypad actuator layer 502, while maintaining a "permanent" bond between the keypad actuator layer 502 and the housing 112. Thus, repeated removal of the graphic keypad overlay 503 should not adversely impact the integrity of the seal between the perimeter area 518 and the sealing rim 510.

Ambient Light Sensor

The fluid infusion device 100 may also include a light sensor 602 that is capable of sensing ambient light levels and providing related output signals to the electronics assembly 122 (see FIG. 33 and FIG. 34). In practice, a light sensor could be located anywhere on the housing 112 or elsewhere on the fluid infusion device 100. For this particular implementation, the light sensor 602 is integrated into the polyimide flex circuitry of the membrane keypad assembly 500. The light sensor 602 is located beneath a partially translucent (dead front) window of the overlying graphic keypad overlay 503, which transmits light. The recorded level of ambient light can be used to control the LED backlight intensity of the LCD display as well as the LED backlight intensity under each of the keypad button icons located on the graphic keypad overlay 503.

Alarm Or Fault LED

The fluid infusion device 100 may also include an alarm/fault LED 604 located on the housing 112, at or near the user interface, or elsewhere. As shown in FIG. 33, the alarm/fault LED 604 may be located underlying the graphic keypad overlay 503. The alarm/fault LED 604 can be activated when the fluid infusion device 100 experiences an alert, alarm, or unrecoverable fault. Depending on the alert/alarm/fault state, the alarm/fault LED 604 might blink at a prescribed frequency, be continuously lit, or flash in a particular pattern. The goal of the alarm/fault LED 604 is to inform the user that an alert, alarm, or fault has occurred and that appropriate action should be taken. For this particular implementation, the alarm/fault LED 604 is integrated into the polyimide flex circuitry of the keypad assembly 500. The alarm/fault LED 604 is located beneath a partially translucent (dead front) window within the overlying graphic keypad overlay 503.

Decorative Back Cover

Figure 35:
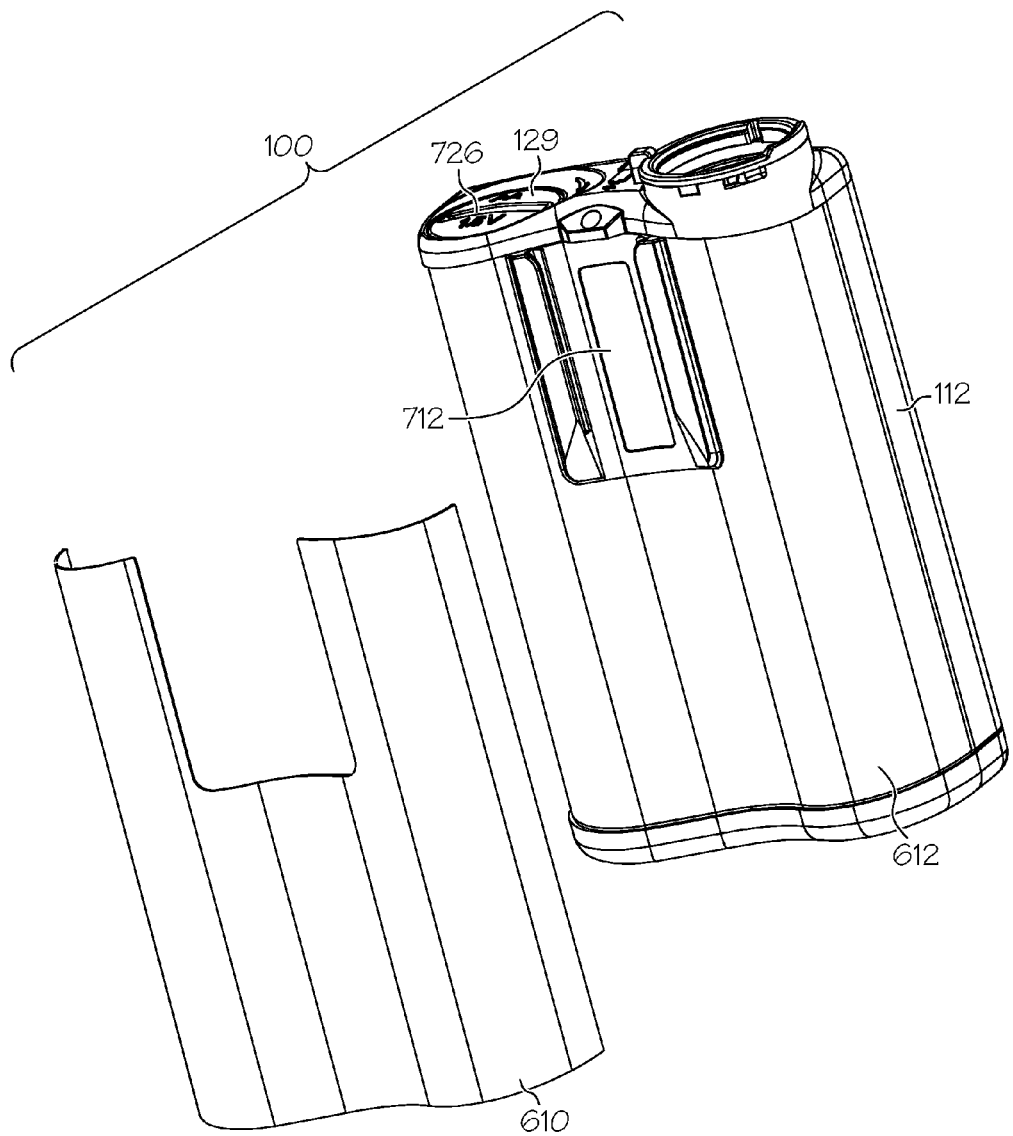
FIG. 35 is a perspective back view of the fluid infusion device prior to installation of a decorative back cover.

The fluid infusion device 100 may also be designed to accommodate a decorative back cover that is applied to the rear surface of the housing 112. In this regard, FIG. 35 is a perspective back view of the fluid infusion device 100 prior to installation of a decorative back cover 610. The decorative back cover 610 can be either a rigid plastic sheet thermoformed to match the curve or contour of the rear surface 612 of the housing 112, or a flexible sheet capable of adapting to the contour of the rear surface 612. The conforming shape of the decorative back cover 610 facilitates easy assembly onto the housing 112.

The decorative back cover 610 is retained on the case with pressure sensitive adhesive, double backed tape, by a press fit engagement, or by a snap fit engagement. The graphics and/or texture of the decorative back cover 610 are customizable and such customization allows generic device assemblies to be created and stocked until such time a stylized decorative back cover 610 is applied to create a specific final assembly. The decorative back cover 610 is designed to be removed and replaced by the end user in the field; thus extra decorative back covers can be made available for purchase by end users.

Belt Clip With Integrated Screwdriver

FIG. 36 is a side view of a belt clip 700 suitable for use with the fluid infusion device 100, and FIG. 37 is an exploded perspective view of the belt clip 700. The illustrated embodiment of the belt clip 700 generally includes, without limitation: a base 702; a mount 704; a spring 706 (only a small portion of which is visible in FIG. 36); and a hinge pin 708. The base 702 and the mount 704 are pivotally coupled together using the hinge pin 708. The hinge pin 708 passes through the body of the spring 706, such that the spring 706 nominally biases the base 702 and the mount 704 toward each other. The belt clip 700 generally functions in accordance with conventional belt clips in that an inward force 710 (see FIG. 36) at the upper ends of the base 702 and the mount 704 will force the lower end of the mount 704 away from the base 702.

The mount 704 is shaped, sized, and configured to mate with a corresponding receptacle 712 integrated in or otherwise located at the back of the fluid infusion device 100 (see FIG. 35). For this particular embodiment, the mount 704 slides into the receptacle and is removably secured therein by a snap fit or a press fit engagement. Thus, the fluid infusion device 100 can be worn by placing the base 702 behind the user's belt, inside the user's pocket, inside the waistline of the user's pants, etc.

The belt clip 700 includes a screwdriver tip integrated therein. The screwdriver tip may be fabricated as part of the base 702 or as part of the mount 704. In certain embodiments, one screwdriver tip could be located on the base 702 and another screwdriver tip could be located on the mount 704. The exemplary embodiment shown in FIG. 36 and FIG. 37 includes a screwdriver tip 720 formed on the base 702. More specifically, the screwdriver tip 720 is formed at the lowermost end 722 of the base 702. The base 702 may be fabricated from a hard and tough molded plastic material such that the screwdriver tip 720 is created as an integrated feature that is continuous and contiguous with the other features of the base 702. Although not always required, the base 702 may be manufactured with reinforcing material or components at or near the screwdriver tip 702 to provide additional structural integrity.

The screwdriver tip 702 is shaped and sized to mate with one or more components or elements of the fluid infusion device 100. For example, the screwdriver tip 702 could be designed to fit an adjustment screw, the battery cap 129 (see FIG. 35), a lock mechanism, or the like. As shown in FIG. 35, the battery cap 129 includes a slot 726 formed therein. The screwdriver tip 702 is shaped and sized to fit this slot 726. Accordingly, when the battery needs to be replaced, the user can simply detach the fluid infusion device 100 from the mount 704, and then use the freed belt clip 700 (more specifically, the screwdriver tip 720) as a screwdriver to remove and replace the battery cap 129 from the housing 112. It should be appreciated that the screwdriver tip can be shaped and sized as desired for purposes of matching the desired features. For example, although the illustrated screwdriver tip 720 is designed to mate with a straight slot, alternate embodiments could be designed to mate with a crosshead slot, a star-shaped hole or cavity, a triangular hole or cavity, or the like.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A shock absorbing element for a battery of a medical device having a battery receptacle for the battery and having an electrical contact for the battery, the electrical contact residing within the battery receptacle, the shock absorbing element composed of a resilient material and comprising:

a perimeter sized and shaped to accommodate placement in the battery receptacle;

a through hole formed in the resilient material, the through hole being sized and shaped to accommodate the electrical contact;

a first side;

a second side; and shock absorbing features formed on the first side or the second side to dissipate kinetic energy associated with motion of the battery relative to the battery receptacle, wherein the shock absorbing features comprise:
a plurality of angled outer depressions, each having a respective high edge near the through hole and having a respective low edge near the perimeter; and
a plurality of angled inner depressions, each having a respective high edge near the perimeter and having a respective low edge near the through hole.

2. The shock absorbing element of claim 1, wherein the shock absorbing element is a one-piece component composed of the resilient material.

3. The shock absorbing element of claim 1, wherein:
the perimeter is generally circular;
the through hole is generally round; and
the perimeter and the through hole are coaxial.

4. The shock absorbing element of claim 3, wherein the shock absorbing features comprise radial ridges formed from the resilient material.

5. The shock absorbing element of claim 3, wherein the shock absorbing features comprise radial depressions formed in the resilient material.

6. The shock absorbing element of claim 1, wherein at least one of the shock absorbing features is formed on the first side, and at least one of the shock absorbing features is formed on the second side.

7. The shock absorbing element of claim 1, wherein:
at least one of the of angled outer depressions is formed on the first side;
at least one of the of angled inner depressions is formed on the first side;
at least one of the of angled outer depressions is formed on the second side; and
at least one of the of angled inner depressions is formed on the second side.

8. The shock absorbing element of claim 7, wherein:
each angled outer depression formed on the first side is aligned with a respective angled inner depression formed on the second side; and
each angled outer depression formed on the second side is aligned with a respective angled inner depression formed on the first side.

9. The shock absorbing element of claim 1, wherein the resilient material is an electrical insulator.

10. A shock absorbing assembly for a battery of a medical device, the shock absorbing assembly comprising:
a battery sleeve to house the battery, the battery sleeve having a base end;
an electrical contact for the battery, the electrical contact residing within the battery sleeve near the base end; and
a shock absorbing element located within the battery sleeve near the base end, the shock absorbing element composed of a resilient material having shock absorbing features integrally formed therein to dissipate kinetic energy associated with motion of the battery toward the base end, wherein the shock absorbing features comprise:
a plurality of angled outer depressions, each having a respective high edge near the through hole and having a respective low edge near the perimeter; and
a plurality of angled inner depressions, each having a respective high edge near the perimeter and having a respective low edge near the through hole.

11. The shock absorbing assembly of claim 10, wherein the shock absorbing element is ring-shaped and surrounds the electrical contact.

12. The shock absorbing assembly of claim 10, wherein the shock absorbing element is attached to the base end.

13. The shock absorbing assembly of claim 10, wherein the shock absorbing element is a one-piece component composed of the resilient material.

14. The shock absorbing assembly of claim 10, wherein the resilient material is an electrical insulator.

15. The shock absorbing assembly of claim 10, wherein the electrical contact comprises an electrically conductive spring.

16. A portable medical device comprising:
a housing;
a battery sleeve inside the housing, the battery sleeve having a base end, wherein the battery sleeve accommodates a battery for the portable medical device;
a battery contact located inside the battery sleeve near the base end; and
a resilient and compressive element located inside the battery sleeve near the base end, the battery contact protruding through the resilient and compressive element, wherein the resilient and compressive element dissipates kinetic energy associated with motion of the battery toward the base end, wherein the resilient and compressive element comprises shock absorbing features integrally formed therein, the shock absorbing features comprising:
a plurality of angled outer depressions, each having a respective high edge near the through hole and having a respective low edge near the perimeter; and
a plurality of angled inner depressions, each having a respective high edge near the perimeter and having a respective low edge near the through hole.

17. The portable medical device of claim 16, wherein the battery sleeve is shaped and sized to accommodate a AA battery.

18. The portable medical device of claim 16, wherein the resilient and compressive element is coupled to the base end such that it resides between the base end and the battery.

19. The portable medical device of claim 16, wherein the battery contact comprises an electrically conductive spring.

20. The portable medical device of claim 16, further comprising infusion pump hardware and an electronics module associated with the infusion pump hardware, wherein the battery serves as a power supply for the infusion pump hardware and the electronics module.

* * * * *

UNITED STATES PATENT AND TRADEMARK OFFICE
CERTIFICATE OF CORRECTION

| | | |
|---|---|---|
| PATENT NO. | : 8,562,565 B2 | Page 1 of 1 |
| APPLICATION NO. | : 12/905931 | |
| DATED | : October 22, 2013 | |
| INVENTOR(S) | : Fonacier et al. | |

It is certified that error appears in the above-identified patent and that said Letters Patent is hereby corrected as shown below:

On the Title Page

Item [75], Delete "Ejmar Fonacier" and insert --EJMar Fonacier--;

Signed and Sealed this
Fifteenth Day of April, 2014

Michelle K. Lee
*Deputy Director of the United States Patent and Trademark Office*